(12) United States Patent
Homan

(10) Patent No.: US 12,107,306 B2
(45) Date of Patent: Oct. 1, 2024

(54) HYDROGEN GENERATOR WITH CARBON CAPTURE FOR USE WITH A HYDROGEN FUEL CELL

(71) Applicant: Clarke G. Homan, Fairport, NY (US)

(72) Inventor: Clarke G. Homan, Fairport, NY (US)

( * ) Notice: Subject to any disclaimer, the term of this patent is extended or adjusted under 35 U.S.C. 154(b) by 0 days.

(21) Appl. No.: 18/233,631

(22) Filed: Aug. 14, 2023

(65) Prior Publication Data

US 2023/0387438 A1 Nov. 30, 2023

Related U.S. Application Data

(63) Continuation of application No. 17/841,012, filed on Jun. 15, 2022, now Pat. No. 11,777,122.

(60) Provisional application No. 63/350,928, filed on Jun. 10, 2022, provisional application No. 63/339,441, filed on May 7, 2022, provisional application No. 63/301,211, filed on Jan. 20, 2022, provisional application No. 63/286,139, filed on Dec. 6, 2021.

(51) Int. Cl.
*H01M 8/0668* (2016.01)
*H01M 8/0656* (2016.01)

(52) U.S. Cl.
CPC ....... *H01M 8/0668* (2013.01); *H01M 8/0656* (2013.01)

(58) Field of Classification Search
CPC .......................... H01M 8/0668; H01M 8/0656
See application file for complete search history.

(56) References Cited

U.S. PATENT DOCUMENTS

| | | | |
|---|---|---|---|
| 5,405,572 A | 4/1995 | DeVolk | |
| 2005/0037245 A1 | 2/2005 | Pham | |
| 2008/0159938 A1 | 7/2008 | Mauthner et al. | |
| 2012/0066966 A1* | 3/2012 | Arne | C10L 1/023 44/452 |
| 2013/0323614 A1 | 12/2013 | Chapman et al. | |
| 2015/0010453 A1 | 1/2015 | Gellett et al. | |
| 2015/0360941 A1 | 12/2015 | Macrae | |
| 2016/0351931 A1 | 12/2016 | Berlowitz et al. | |
| 2017/0341936 A1 | 11/2017 | Wasserscheid et al. | |
| 2022/0298091 A1* | 9/2022 | Okolo | C07C 29/86 |

FOREIGN PATENT DOCUMENTS

| | | |
|---|---|---|
| WO | WO2021189137 | 9/2021 |
| WO | WO2023053149 | 4/2023 |

OTHER PUBLICATIONS

International Search Report With Written Opinion for PCT/US2022/051980 Jun. 27, 2023.

* cited by examiner

*Primary Examiner* — Olatunji A Godo
(74) *Attorney, Agent, or Firm* — Michael J. Nickerson

(57) ABSTRACT

A hydrogen generator includes a gasifier, upon receiving steam and methane, configured to convert the methane and steam into hydrogen and carbon monoxide; and a carbon trap, operatively connected to the gasifier, configured to capture carbon from the carbon monoxide and allow the hydrogen to pass therethrough. The carbon trap includes iron and a heat source.

7 Claims, 20 Drawing Sheets

HYDROGEN GENERATOR WITH CARBON CAPTURE FOR USE WITH A HYDROGEN FUEL CELL

PRIORITY INFORMATION

The present application is a continuation-in-part of U.S. patent application Ser. No. 17/841,012, filed on Jun. 15, 2022 and claims priority, under 35 U.S.C. § 120, from U.S. patent application Ser. No. 17/841,012, filed on Jun. 15, 2022; said U.S. patent application Ser. No. 17/841,012, filed on Jun. 15, 2022 claiming priority, under 35 U.S.C. § 119(e), from U.S. Provisional Patent Application, Ser. No. 63/286,139, filed on Dec. 6, 2021; said U.S. patent application Ser. No. 17/841,012, filed on Jun. 15, 2022 claiming priority, under 35 U.S.C. § 119(e), from U.S. Provisional Patent Application, Ser. No. 63/301,211, filed on Jan. 20, 2022; said U.S. patent application Ser. No. 17/841,012, filed on Jun. 15, 2022 claiming priority, under 35 U.S.C. § 119(e), from U.S. Provisional Patent Application, Ser. No. 63/339,441, filed on May 7, 2022; said U.S. patent application Ser. No. 17/841,012, filed on Jun. 15, 2022 claiming priority, under 35 U.S.C. § 119(e), from U.S. Provisional Patent Application, Ser. No. 63/350,928, filed on Jun. 10, 2022. The entire content of U.S. patent application Ser. No. 17/841,012, filed on Jun. 15, 2022, is hereby incorporated by reference.

The present application claims priority, under 35 U.S.C. § 119(e), from U.S. Provisional Patent Application, Ser. No. 63/286,139, filed on Dec. 6, 2021. The entire content of U.S. Provisional Patent Application, Ser. No. 63/286,139, filed on Dec. 6, 2021, is hereby incorporated by reference.

The present application claims priority, under 35 U.S.C. § 119(e), from U.S. Provisional Patent Application, Ser. No. 63/301,211, filed on Jan. 20, 2022. The entire content of U.S. Provisional Patent Application, Ser. No. 63/301,211, filed on Jan. 20, 2022, is hereby incorporated by reference.

The present application claims priority, under 35 U.S.C. § 119(e), from U.S. Provisional Patent Application, Ser. No. 63/339,441, filed on May 7, 2022. The entire content of U.S. Provisional Patent Application, Ser. No. 63/339,441, filed on May 7, 2022, is hereby incorporated by reference.

The present application claims priority, under 35 U.S.C. § 119(e), from U.S. Provisional Patent Application, Ser. No. 63/350,928, filed on Jun. 10, 2022. The entire content of U.S. Provisional Patent Application, Ser. No. 63/350,928, filed on Jun. 10, 2022, is hereby incorporated by reference.

BACKGROUND

Conventional hydrogen fuel cells utilize hydrogen to generate electricity. As illustrated in FIG. 1, a hydrogen fuel cell 100 is constructed of an anode 110 containing a catalyst, a proton exchange membrane 120, and a cathode 130. An electrical load 10 is connected across the anode 110 and cathode 130.

Hydrogen ($H_2$) is introduced to the anode 110 containing a catalyst, which strips the electrons from the hydrogen. The striped electrons travel to the cathode 130, via load 10. The excess protons ($H^+$) from the anode 110 migrate across the proton exchange membrane 120 to the cathode 130, wherein the protons and electrons are reunited to create hydrogen. Air can be introduced in an optional chamber 140 to create water and heat.

Hydrogen fuel cells, to operate, need a source of hydrogen. Conventionally, hydrogen fuel cell is fed hydrogen created by a hydrogen generator that converts methanol ($CH_3OH$).

FIG. 2 illustrates a conventional arrangement of a hydrogen generator 20 feeding a hydrogen fuel cell. As illustrated in FIG. 2, a source 200 of methane 250 enters the hydrogen generator 20 and feeds a gasifier 300. The gasifier 300 uses steam 275 to convert the methane into a metastable mixture of hydrogen 325 and carbon monoxide. The metastable gas forms a stable gas mixture of methanol 260 and hydrogen 325. The stable gas mixture of methanol 260 and hydrogen 325 is fed to a condenser 310, which produces liquid methanol 265, heat, and hydrogen 325. The hydrogen 325 is fed to a hydrogen fuel cell 100 that converts the hydrogen to electrical power.

The hydrogen generator 20 of FIG. 2 is an ideal generator assuming that the number of methane molecules equals the number of steam molecules in the gasifier. Normally, the number of methane molecules in the gasifier varies with time since the natural gas source composition varies in methane content.

The operator can control the process, either by burning (flaring) some of the methane supply releasing carbon dioxide to the atmosphere or by adjusting the steam flow or both. The product of this ideal process produces "green" methanol and hydrogen.

If the operator supplies less steam than the methane supply in the gasifier, the gasifier and condenser will supply "green" methanol, hydrogen and excess methane. This process can be called the "green" methanol process. "Green" methanol is defined as methanol having very low water content since methanol is hydroscopic. If the hydrogen and excess methane is supplied to a hydrogen fuel cell, the cell produces electrical power, but emits methane to the atmosphere.

If the operator supplies more steam than the methane supply, the gasifier and condenser will supply a liquid solution of water and methanol. If this liquid solution is gasified, it produces carbon dioxide and hydrogen. This process can be called the "red" methanol process and is to be avoided for reasons discussed below. "Red" methanol is defined as methanol having large water content since the gaseous methanol condenses with the excess water (steam) in the condenser. If the carbon dioxide and hydrogen from the "red" process is supplied to a hydrogen fuel cell, the cell produces electrical power, but emits carbon dioxide to the atmosphere.

FIG. 3 illustrates another conventional arrangement of a hydrogen generator feeding a hydrogen fuel cell. As illustrated in FIG. 3, a source of methanol 265 feeds a vaporizer 315. The vaporizer 315 vaporizes the methanol 265 into carbon monoxide 375 and hydrogen 325. The gas mixture of carbon monoxide 375 and hydrogen 325 is fed to a hydrogen fuel cell 100 that converts the hydrogen to electrical power, but emits toxic carbon monoxide 375.

As described above, the conventional sources of hydrogen for a hydrogen fuel cell can create various undesirable by-products, such as carbon monoxide.

Therefore, it is desirable to provide a source of hydrogen for a hydrogen fuel cell that minimizes or eliminates the undesirable by-products.

Therefore, it is further desirable to provide a source of hydrogen for a hydrogen fuel cell that minimizes or eliminates the undesirable by-product of carbon monoxide.

It is also desirable to provide a source of hydrogen for a hydrogen fuel cell that utilizes methane as a source from which to derive hydrogen.

Furthermore, it is desirable to provide a source of hydrogen for a hydrogen fuel cell that utilizes methane as a source from which to derive hydrogen and minimizes or eliminates the undesirable by-products.

Also, it is desirable to provide a source of hydrogen for a hydrogen fuel cell that utilizes methane as a source from which to derive hydrogen and minimizes or eliminates the by-product carbon monoxide.

Moreover, it is desirable to provide a source of hydrogen for a hydrogen fuel cell that utilizes methane and/or methanol as sources from which to derive hydrogen.

Additionally, it is desirable to provide a source of hydrogen for a hydrogen fuel cell that utilizes methane and/or methanol as sources from which to derive hydrogen and minimizes or eliminates the undesirable by-products.

Lastly, it is desirable to provide a source of hydrogen for a hydrogen fuel cell that utilizes methane and/or methanol as sources from which to derive hydrogen and minimizes or eliminates the by-product carbon monoxide.

Furthermore, it is desirable to provide a process that converts "red" methanol to "green" methanol.

BRIEF DESCRIPTION OF THE DRAWINGS

The drawings are only for purposes of illustrating various embodiments and are not to be construed as limiting, wherein.

DETAILED DESCRIPTION

Figure 1:
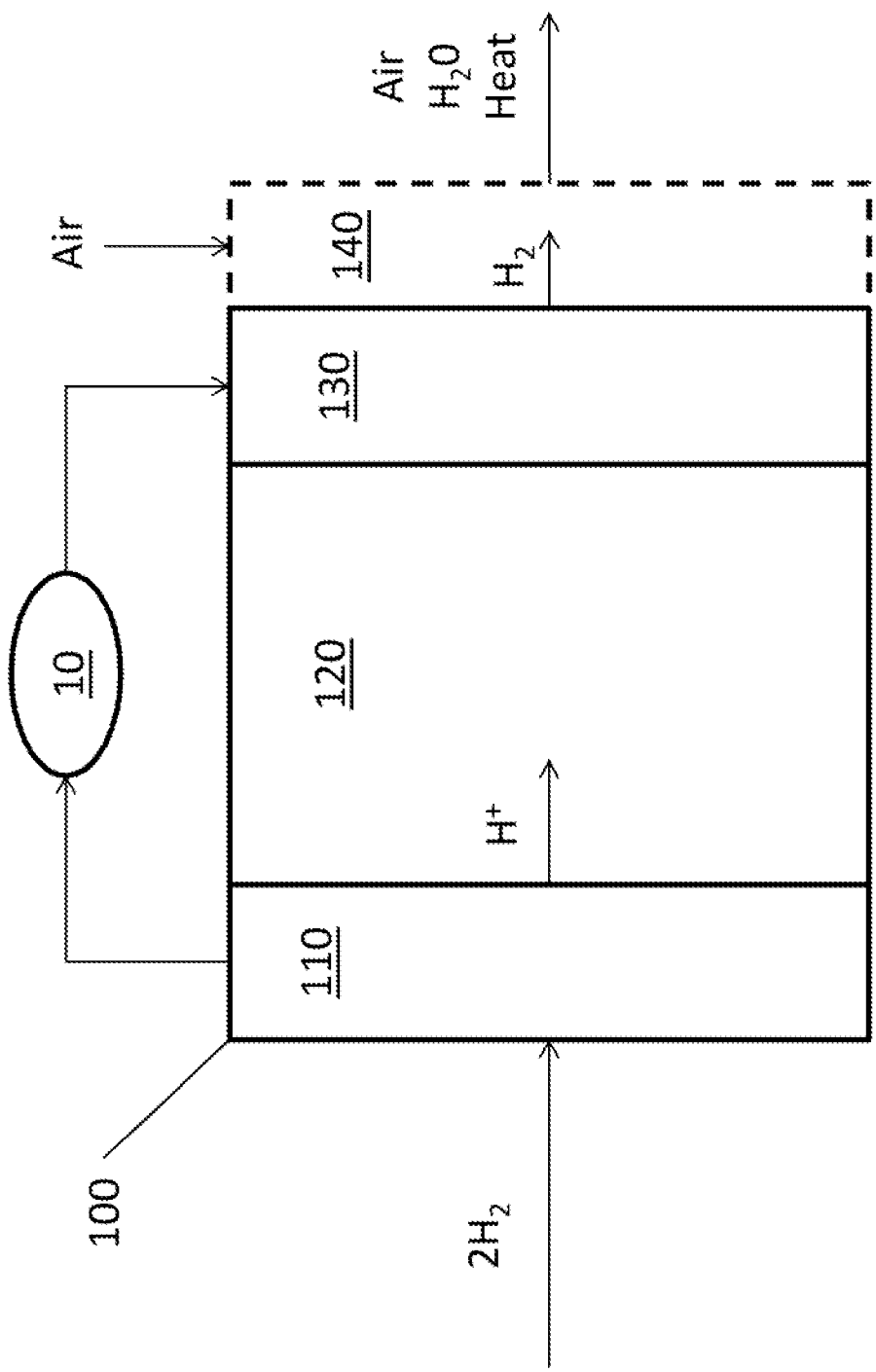
FIG. 1 illustrates a conventional hydrogen fuel cell.
Figure 2:
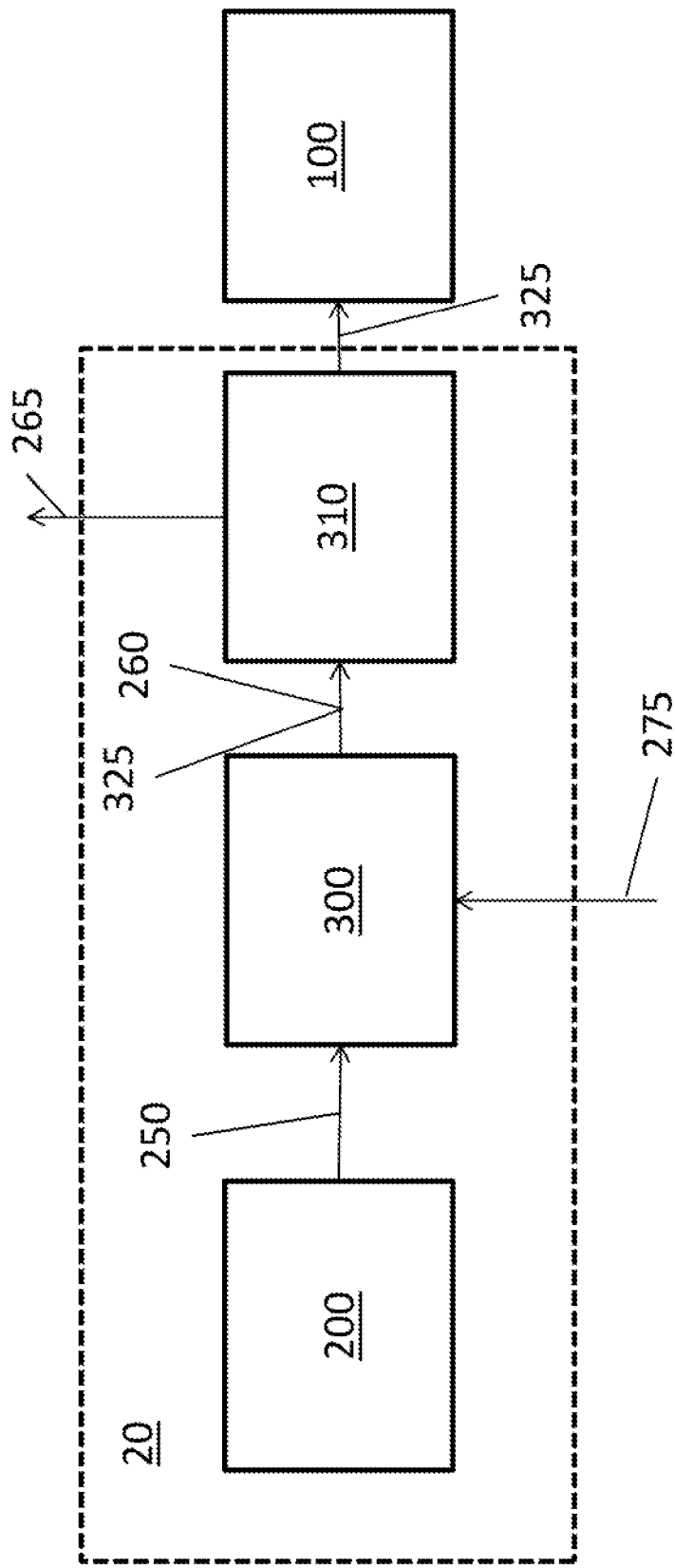
FIG. 2 illustrates a conventional arrangement of a hydrogen generator feeding a hydrogen fuel cell.
Figure 3:
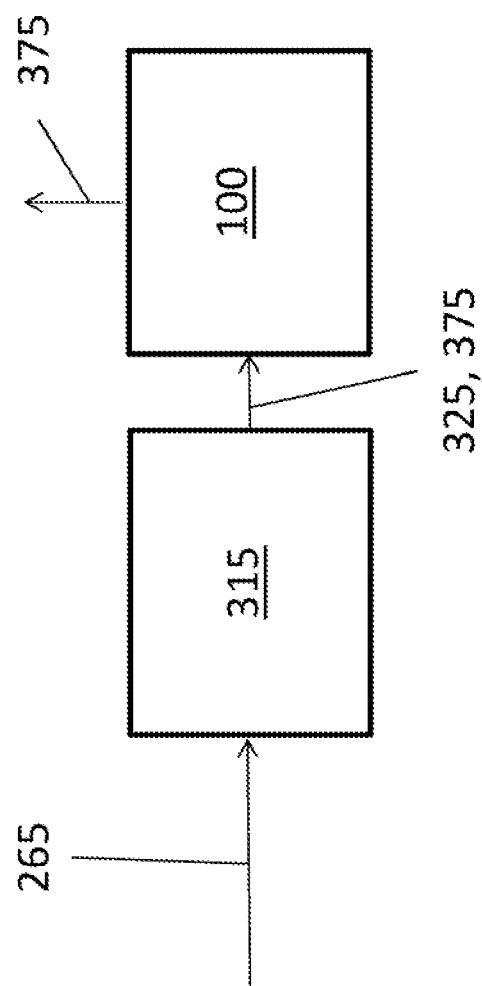
FIG. 3 illustrates another conventional arrangement of a hydrogen generator feeding a hydrogen fuel cell.

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts may be properly illustrated.

Figure 4:
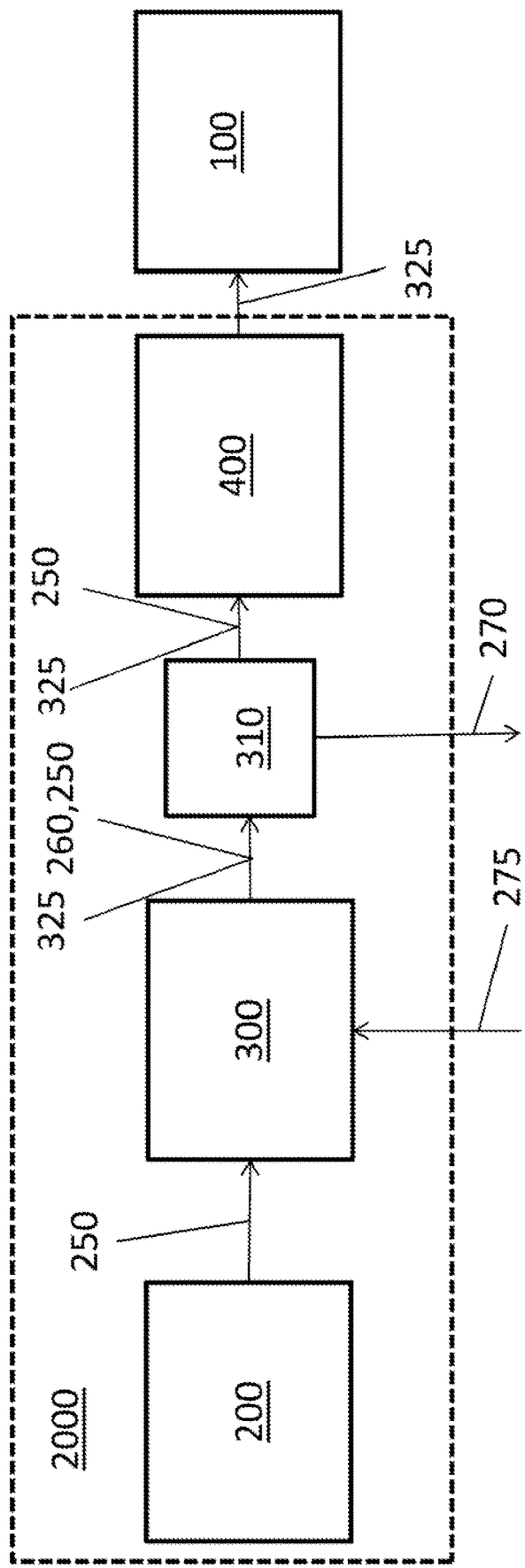
FIG. 4 illustrates an arrangement of a hydrogen generator that utilizes methane to create hydrogen to feed to a hydrogen fuel cell.

FIG. 4 illustrates an arrangement of a hydrogen generator 2000 that utilizes methane to create hydrogen to feed to a hydrogen fuel cell. As illustrated in FIG. 4, the hydrogen generator 2000 includes a source 200 of methane 250 that feeds a gasifier 300. The gasifier 300 uses steam 275 to convert the methane into methanol 260, hydrogen 325, and excess methane 250.

The methanol 260, hydrogen 325, and excess methane 250 is fed to a condenser 310 which produces liquid methanol 270, hydrogen 325, and excess methane 250. The liquid methanol 270 is drained from the condenser 310 for use in other applications.

The hydrogen 325 and excess methane 250 is fed to a carbon trap 400 that captures the carbon from the excess methane 250 to create hydrogen. The carbon from the excess methane 250 is trapped in iron.

The hydrogen 325 is fed to a hydrogen fuel cell 100, which converts the hydrogen 450 into electricity.

Figure 5:
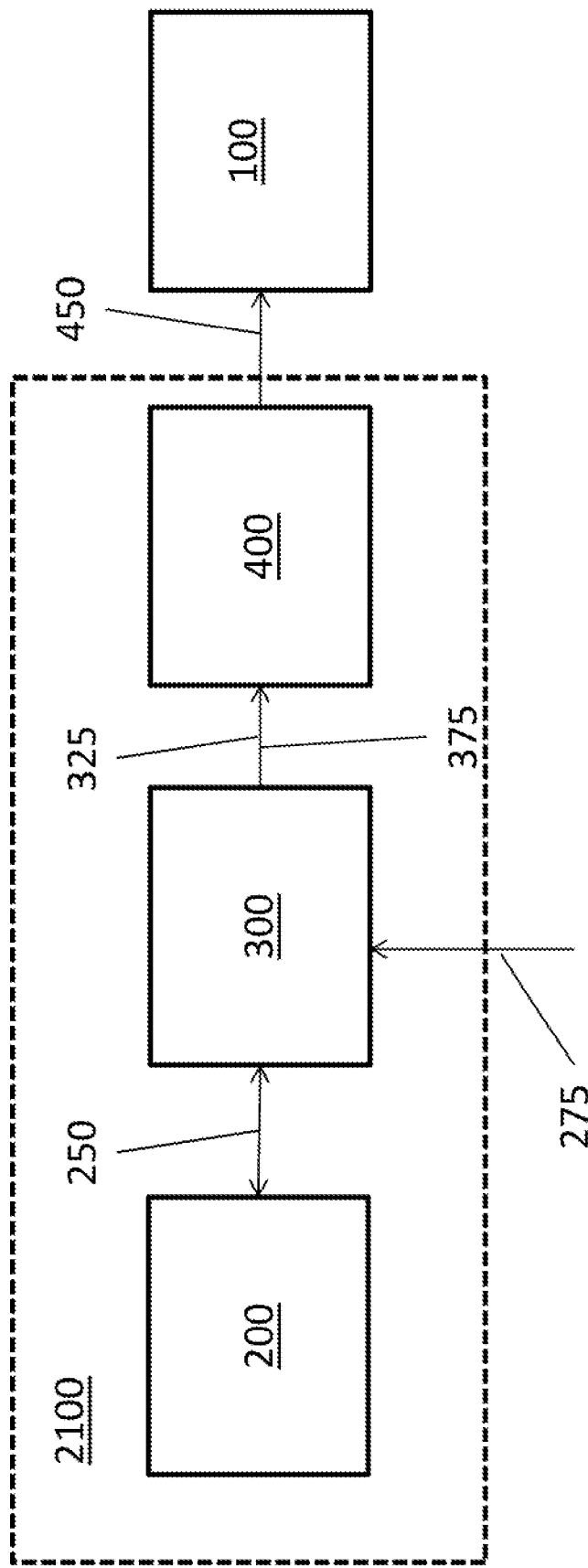
FIG. 5 illustrates another arrangement of a hydrogen generator that utilizes methane to create hydrogen to feed to a hydrogen fuel cell.

FIG. 5 illustrates another arrangement of a hydrogen generator 2100 that utilizes methane to create hydrogen to feed to a hydrogen fuel cell. As illustrated in FIG. 5, the hydrogen generator 2100 includes a source 200 of methane 250 that feeds a gasifier 300. The gasifier 300 uses steam 275 to convert the methane into hydrogen 325 and carbon monoxide 375.

The hydrogen 325 and carbon monoxide 375 is fed to a carbon trap 400 that captures the carbon from the carbon monoxide 375 to create oxygen. The carbon from the carbon monoxide 375 is trapped in iron.

Hydrogen 450 is passed through the carbon trap 400 and is fed to a hydrogen fuel cell 100, which converts the hydrogen 450 into electricity.

Figure 6:
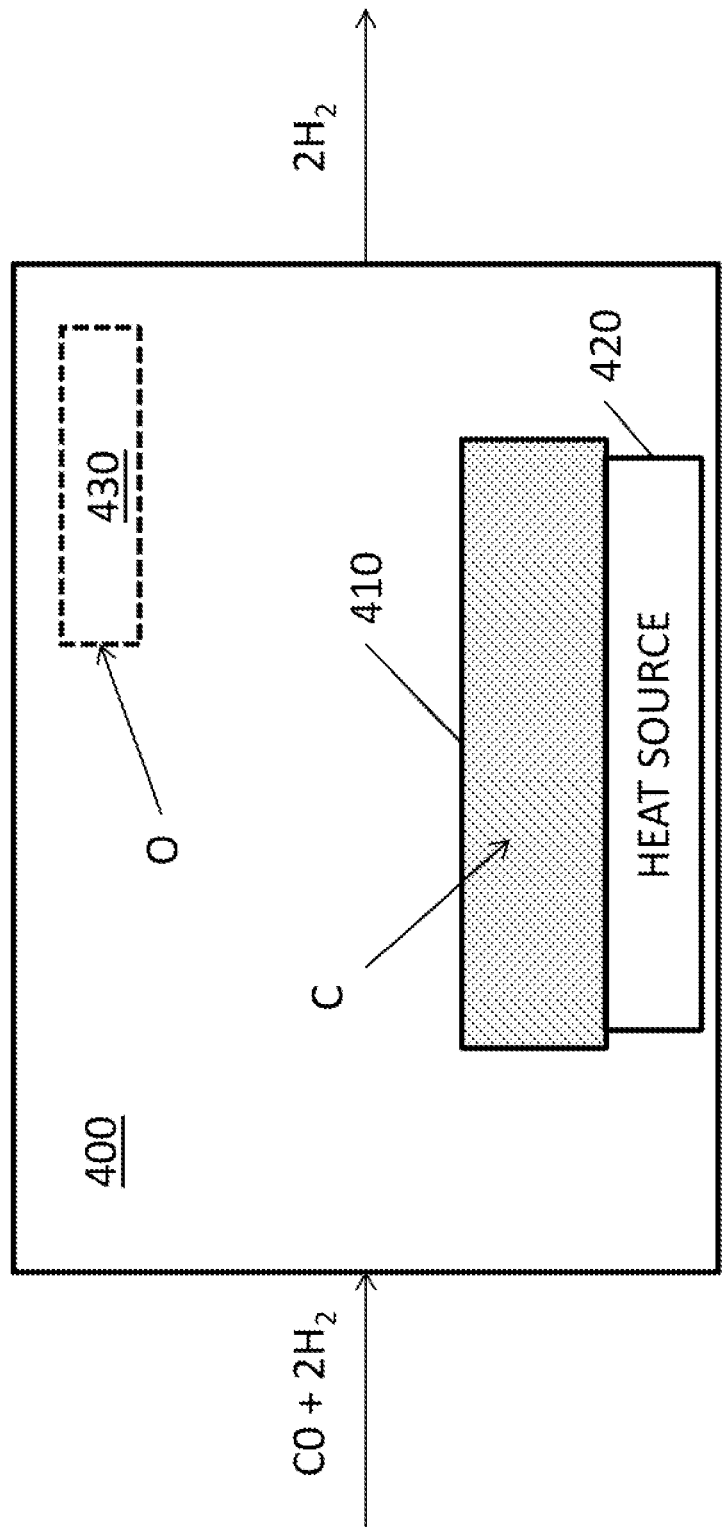
FIGS. 6 and 7 illustrate a carbon trap.

FIG. 6 illustrates a carbon trap. As illustrated in FIG. 6, a carbon trap 400 includes a source 410 of iron (Fe) and a heat source 420. If carbon monoxide and hydrogen are introduced into the carbon trap 400, the source 410 of iron (Fe) is carbonized by the carbon in the carbon monoxide to produce oxygen.

In other words, the carbon monoxide is converted to carbon and oxygen, with the carbon being trapped in the source 410 of iron (Fe) and the oxygen being available to be released to the atmosphere or captured for other uses.

The carbon trap 400 may include an optional oxygen trap 430, which may be a heated source of copper. The oxygen trap 430 captures the oxygen from carbonization process, yielding hydrogen flow that can be fed to a hydrogen fuel cell.

The carbon trap 400 can be loaded with pure iron. Within the carbon trap 400, the iron can be levitated off a support (not shown) using an induction coil (heat source 420) and a copper "mirror" (not shown) to a stable position. Increasing the induction power, heats the iron to a desired carburizing temperature. More specifically, the C—Fe eutectoid temperature is less than 723° K.

The hydrogen gas is unchanged by the carbon trap 400. The result is the conversion of the carbon monoxide and hydrogen gasses into carbon stored in the iron 410 and a mixture of hydrogen and oxygen gasses. The rate at which the iron 410 can absorb carbon is dependent on the surface area of the iron 410, the rate of absorption of carbon on the surface of iron 410, the rate of diffusion of the carbon into the iron's volume, and the optimal carbon content in the iron 410 for efficient operation. The rate of diffusion of the carbon in iron 410, the optimal carbon content, and the rate of absorption of carbon at the surface depend on the operating temperature of the iron 410.

When the carburized iron cannot usefully capture carbon supplied by the carbon monoxide, the carburized iron can be easily replaced with another source of iron 410. The used carburized iron can easily be recycled for other purposes or safely disposed.

Figure 7:
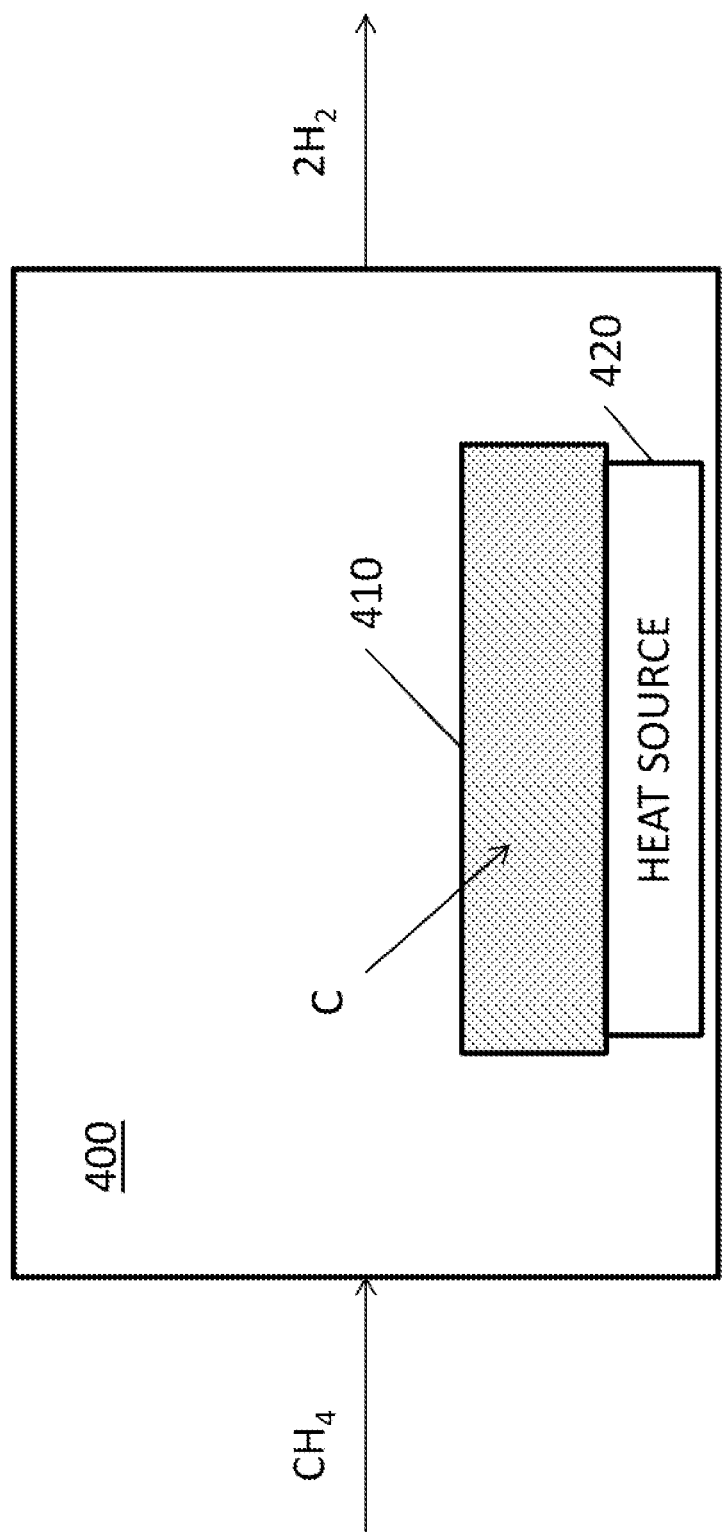

FIG. 7 illustrates a carbon trap wherein methane is introduced therein. As illustrated in FIG. 7, a carbon trap 400 includes a source 410 of iron (Fe) and a heat source 420. Methane ($CH_4$) introduced into the carbon trap 400. The iron 410 is carbonized by the carbon in the methane. In other words, the methane is converted to carbon and hydrogen, with the carbon being trapped in the source 410 of iron (Fe) and the hydrogen being available to be fed to a hydrogen fuel cell.

The carbon trap 400 can be loaded with pure iron 410. Within the carbon trap 400, the iron 410 can be levitated off a support (not shown) using an induction coil (heat source 420) and a copper "mirror" (not shown) to a stable position. Increasing the induction power, heats the iron 410 to a desired carburizing temperature. More specifically, the C—Fe eutectoid temperature is less than 723° K.

Figure 8:
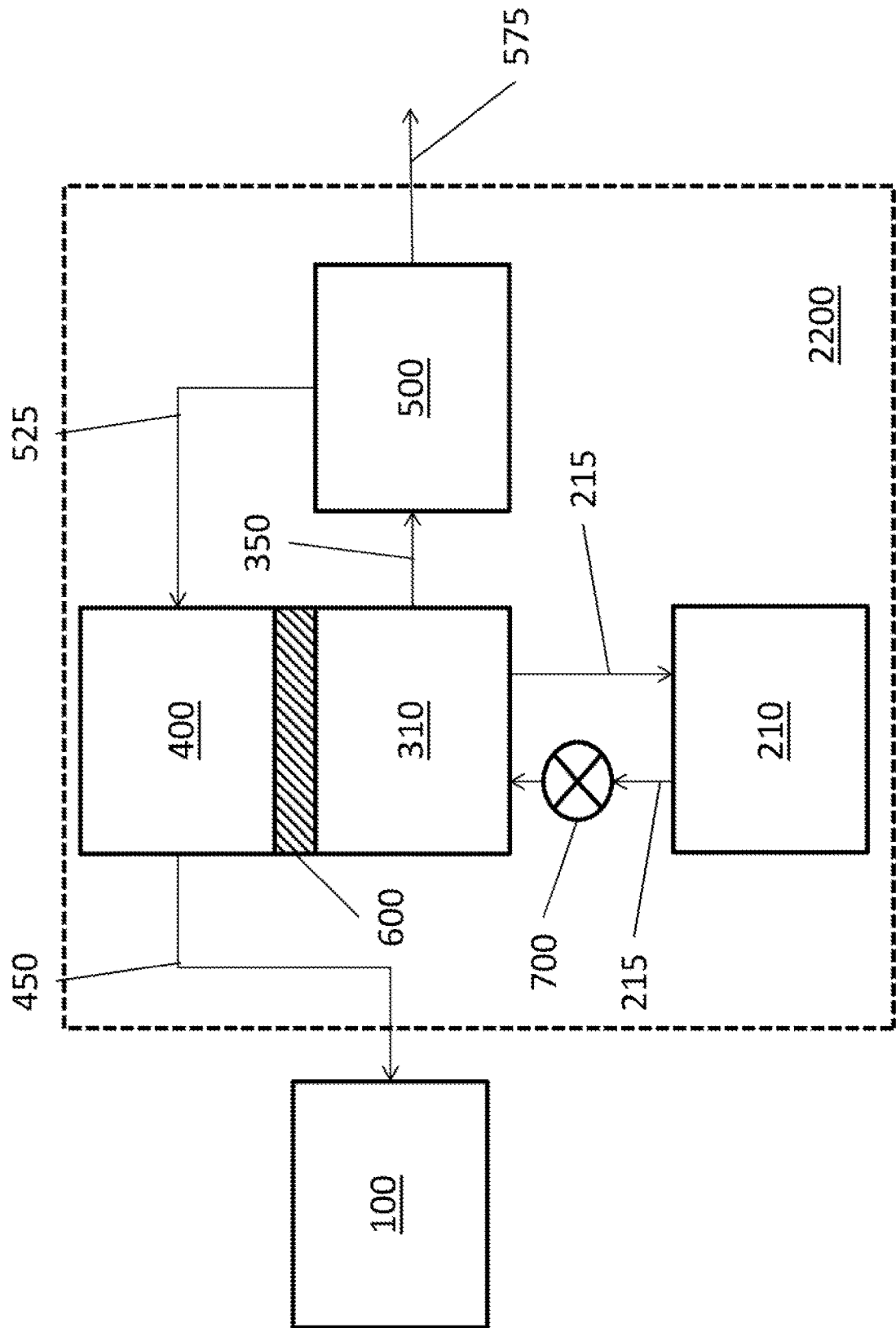
FIG. 8 illustrates an arrangement of a hydrogen generator that utilizes methanol to create hydrogen to feed to a hydrogen fuel cell.

FIG. 8 illustrates another arrangement of a hydrogen generator 2200 that utilizes methanol to generate hydrogen to feed to a hydrogen fuel cell. As illustrated in FIG. 8, the hydrogen generator 2200 includes a source 210 of methanol 215. The methanol 215 is fed to a vaporizer 310, via valve 700. The vaporizer 310 uses heat to convert the liquid methanol 215 into a combination of methane gas and water vapor (350).

Any excess liquid methanol 215 is returned to the source 210 of methanol 215. The combination of methane and water vapor (350) is fed into a condenser 500 to remove the water vapor from the methane by cooling the combination so that the water vapor condenses to liquid water (575) and can be removed via a drain (not shown). Water condenses between 80° C. and 100° C., whereas methane condenses below 80° C. In other words, the liquid/gas temperature boundary of water is much higher than such that methane is a gas when water vapor has condensed into a liquid.

The methane 525 from condenser 500 is fed to a carbon trap 400 that captures the carbon from the methane 525 to create hydrogen 450. The carbon from the methane 525 is trapped in iron.

Hydrogen 450 is passed through the carbon trap 400 and is fed to a hydrogen fuel cell 100, which converts the hydrogen 450 into electricity.

As illustrated in FIG. 8, a heat source 600 is shared by the vaporizer 310 and the carbon trap 400 such that heat source 600 provides heat to activate the iron in the carbon trap 400 and heat to the vaporizer 310 to enable the convert the liquid methanol 215 into a combination of methane gas and water vapor (350).

Figure 9:
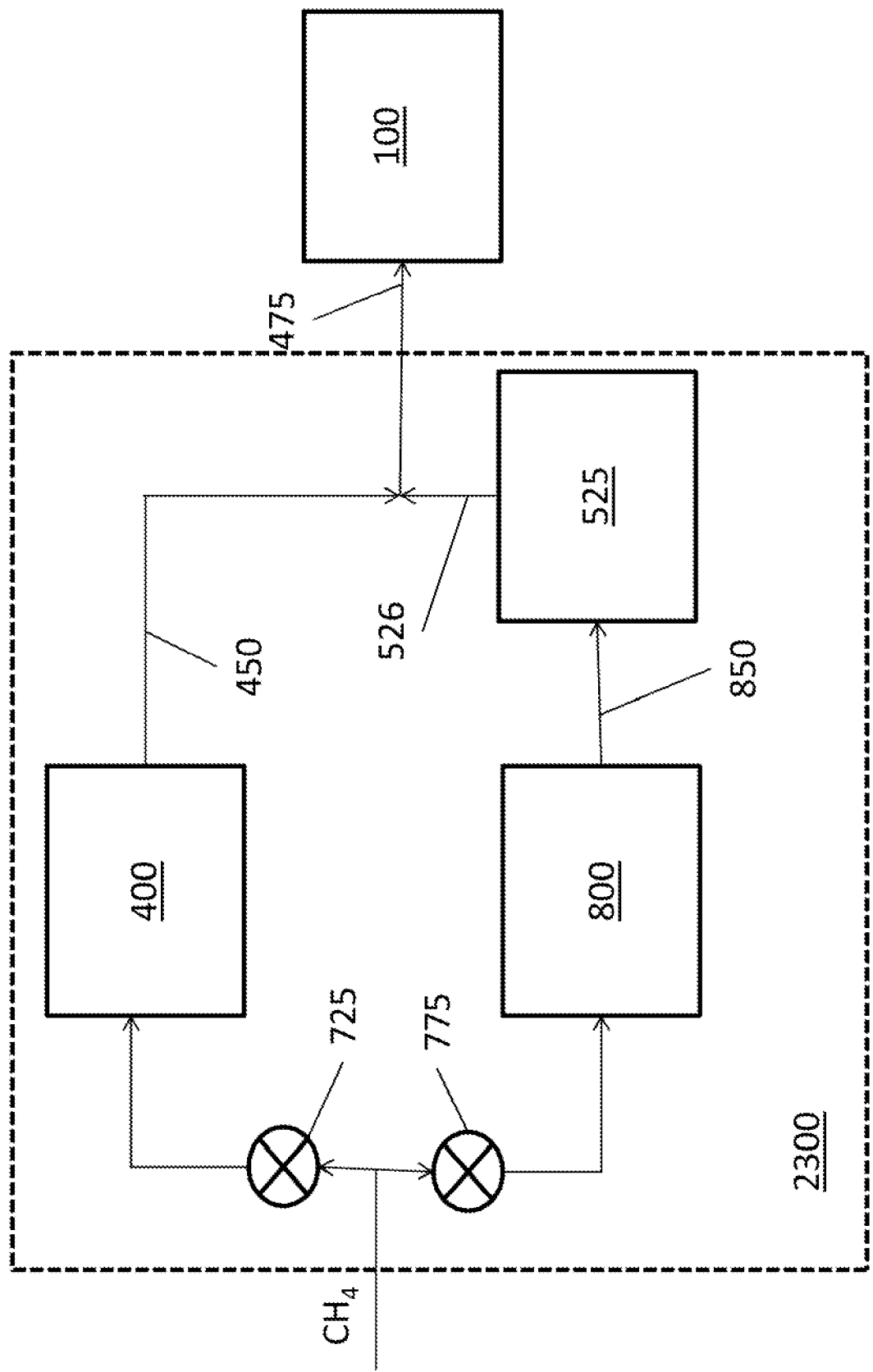
FIG. 9 illustrates another arrangement of a hydrogen generator that utilizes methane to create hydrogen to feed to a hydrogen fuel cell.

FIG. 9 illustrates another arrangement of a hydrogen generator 2300 that utilizes methane to create hydrogen to feed to a hydrogen fuel cell. As illustrated in FIG. 9, the hydrogen generator 2300 includes a source of methane (not shown). The flow of the methane is controlled by valves 725 and 775.

Methane is fed through valve 725 to a carbon trap 400 that captures the carbon from the methane to create hydrogen 450. The carbon from the methane is trapped in iron. Hydrogen 450 is passed through the carbon trap 400 and is fed to a hydrogen fuel cell 100, which converts the hydrogen 475 into electricity.

Methane is also fed through valve 775 to a gasifier 800 that mixes the methane with steam (water vapor) to create carbon monoxide (gas) and hydrogen (gas). The combination of carbon monoxide (gas) and hydrogen (gas) is fed to a methanization module 525 that produces liquid methanol and hydrogen.

The hydrogen 475 from the carbon trap 400 and the hydrogen 526 from the methanization module 525 are combined to a flow of hydrogen 475, which is fed to the hydrogen fuel cell 100 and is converted into electricity.

Figure 10:
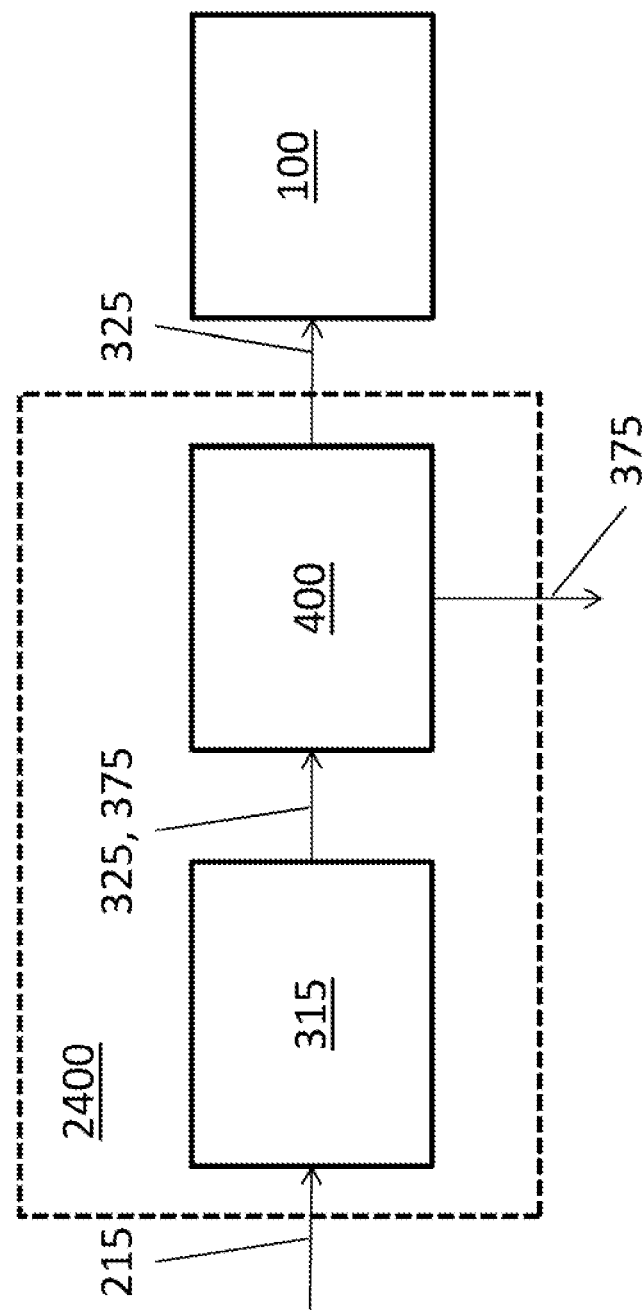
FIG. 10 illustrates another arrangement of a hydrogen generator that utilizes methanol to generate hydrogen to feed to a hydrogen fuel cell.

FIG. 10 illustrates an arrangement of a hydrogen generator 2400 that utilizes methanol 215 to generate hydrogen to feed to a hydrogen fuel cell 100. Methanol 215 is fed to a vaporizer 315 to produce carbon monoxide 375 and hydrogen 325. This mixture is passed through a carbon trap 400. The carbon is captured from the carbon monoxide and stored in the iron of the carbon trap 400. If an oxygen trap is included in the carbon trap 400, the resultant flow of hydrogen (and uncaptured oxygen) is fed to a hydrogen fuel 100 producing energy.

Figure 11:
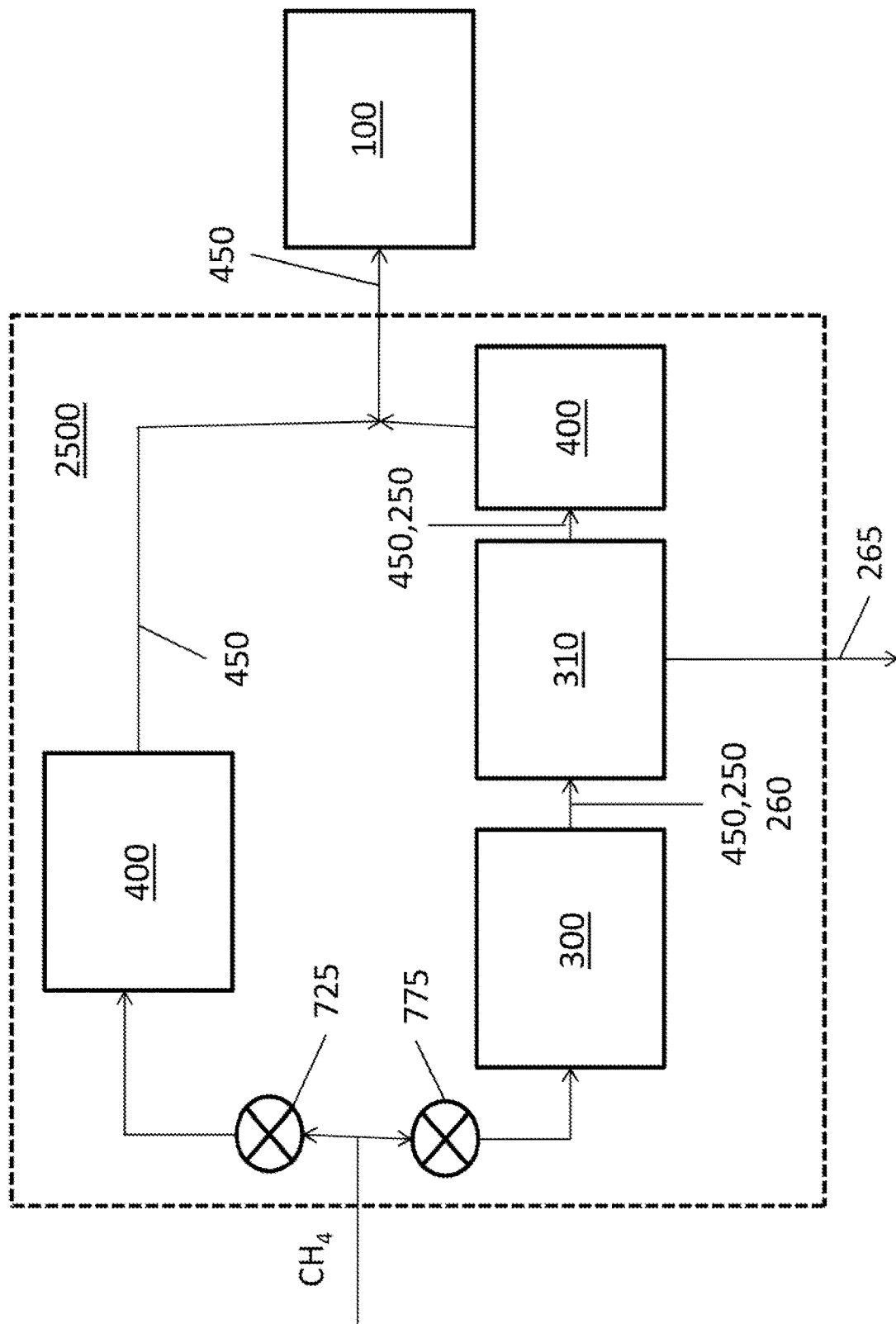
FIG. 11 illustrates another arrangement of a hydrogen generator that utilizes methane to create hydrogen to feed to a hydrogen fuel cell.

FIG. 11 illustrates another arrangement of a hydrogen generator 2500 that utilizes methane to create hydrogen to feed to a hydrogen fuel cell 100. As illustrated in FIG. 11, the hydrogen generator 2500 includes a source of methane (not shown). The flow of the methane is controlled by valves 725 and 775.

Methane is fed through valve 725 to a carbon trap 400 that captures the carbon from the methane to create hydrogen 450. The carbon from the methane is trapped in the iron located in the carbon trap 400. Hydrogen 450 is passed through the carbon trap 400 and is fed to a hydrogen fuel cell 100, which converts the hydrogen 450 into electricity.

Methane is also fed through valve 775 to a gasifier 300 that mixes the methane with steam (water vapor) to create hydrogen 450, methanol 260, and methane gas 250 which is passed through a condenser 310. The condenser 310 liquefies the methanol 265 and provides hydrogen 450 and methane to a carbon trap 400 that captures the carbon from the methane to create hydrogen 450. The hydrogen 450 from the carbon trap 400 is fed to the hydrogen fuel cell 100. The liquified methanol 265 may be stored for later use.

Figure 12:
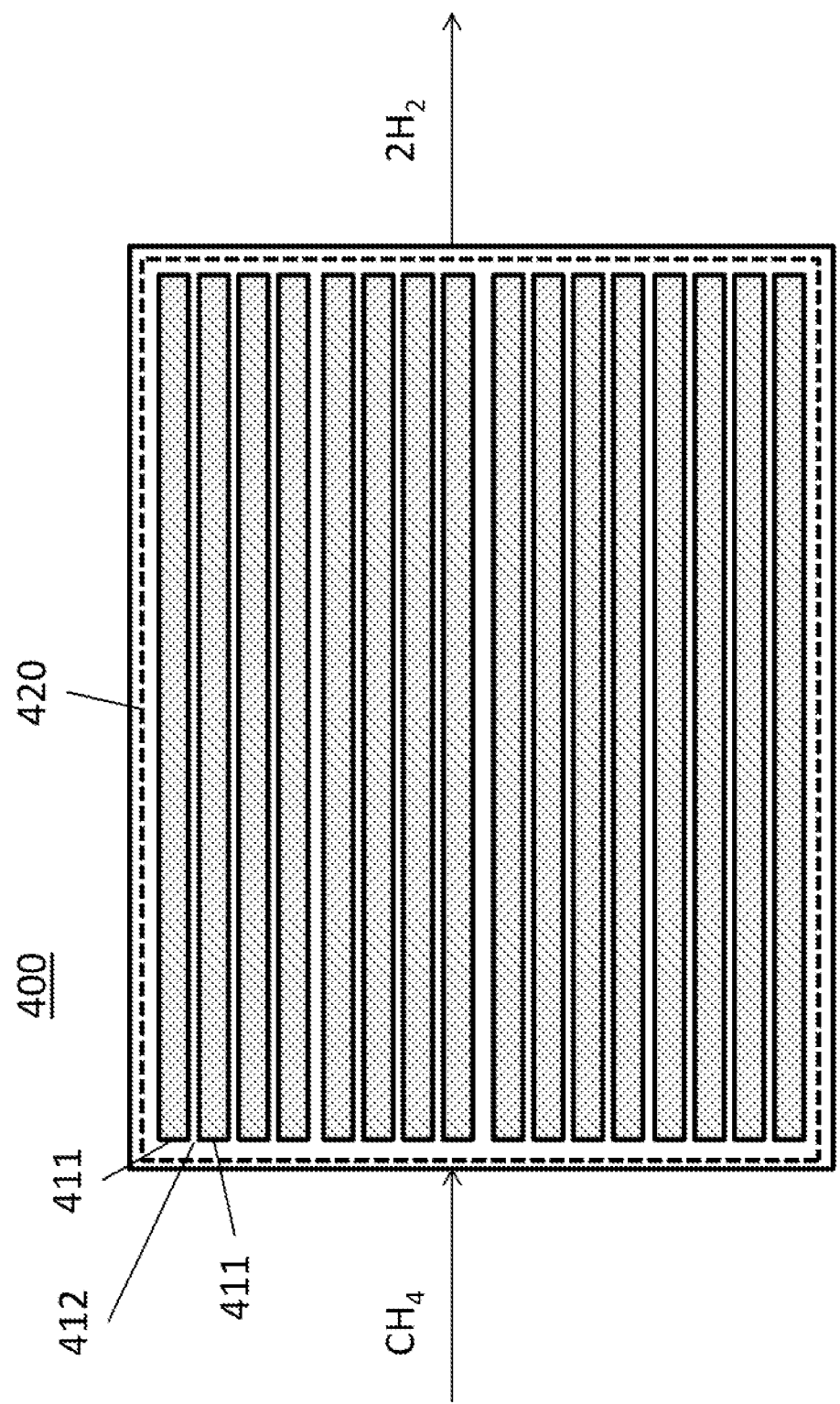
FIG. 12 illustrates an arrangement of a carbon trap.

FIG. 12 illustrates an arrangement of a carbon trap. As illustrated in FIG. 12, the carbon trap 400 includes multiple parallel planes (411) of iron that form channels (412) for methane, as illustrated, to flow therethrough. The channels 412 increase the surface area of the iron that can be exposed to the methane. The increased surface area increases the capture of the carbon. It is noted that the surface area to volume ratio of the iron should be maximized to increase the capture of the carbon.

It is noted that a combination of carbon monoxide and hydrogen can also utilize the carbon trap 400 of FIG. 12.

It is further noted that the multiple parallel planes (411) of iron may be located in a carbon trap module 420 so that the entire carbon trap 400 does not need to be replaced, when the iron becomes too saturated to trap carbon, only the carbon trap module 420. The carbon trap module 420 and its contents may be heated independently, minimizing the heat loss from conduction to the carbon trap 400.

Figure 13:
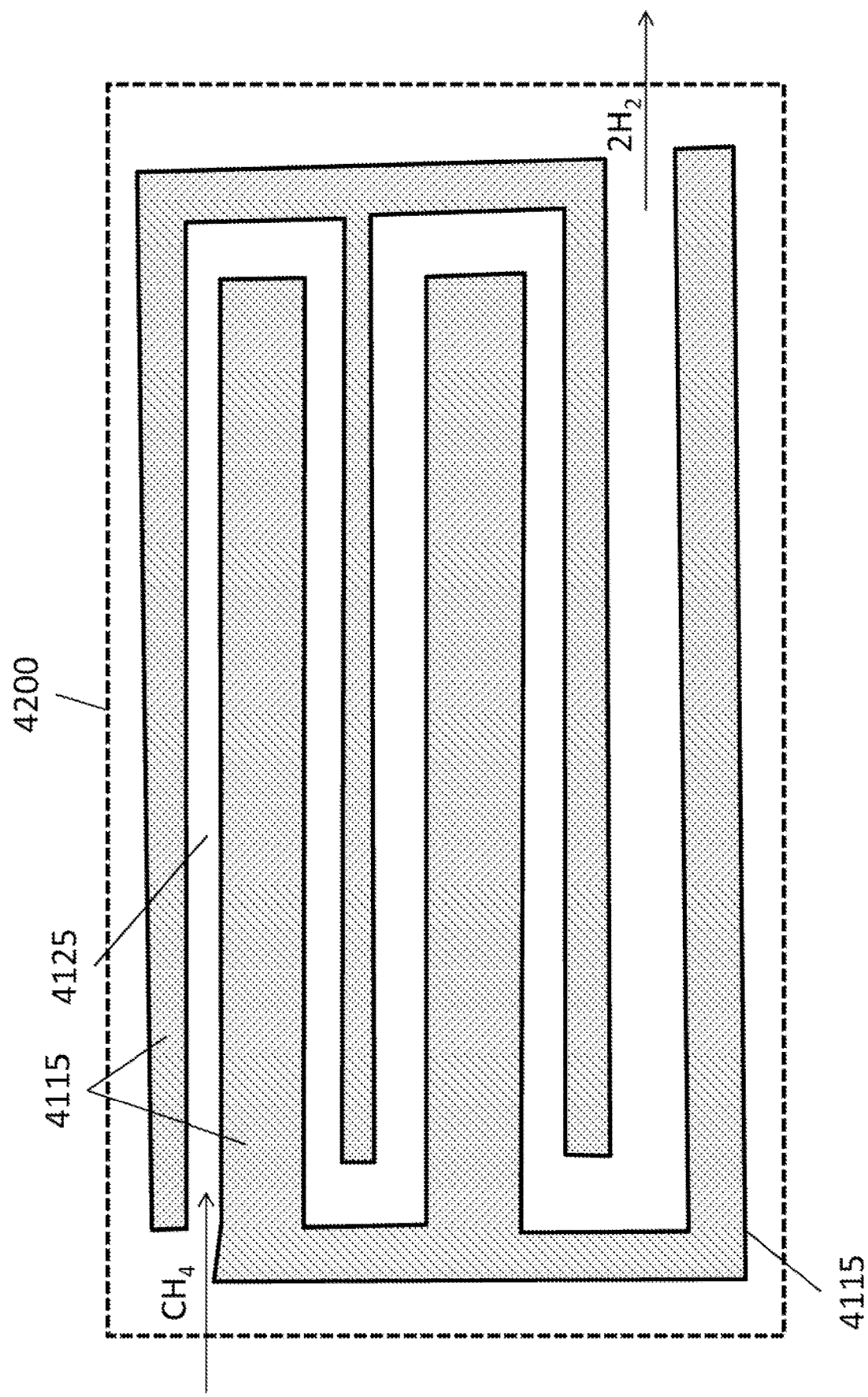
FIG. 13 illustrates another arrangement of a carbon trap module.

FIG. 13 illustrates another arrangement of a carbon trap module. As illustrated in FIG. 13, the carbon trap module 4200 includes fingered planes (4115) of iron that form a serpentine channel (4125) for methane, as illustrated, to flow therethrough. The serpentine channel 4125 increases the surface area of the iron that can be exposed to the methane. The increased surface area increases the capture of the carbon. It is noted that the surface area to volume ratio of the iron should be maximized to increase the capture of the carbon.

It is noted that a combination of carbon monoxide and hydrogen can also utilize the carbon trap module 4200 of FIG. 13.

It is further noted that the carbon trap module 4200 can be replaced without replacing the entire carbon trap 40, when the iron becomes too saturated to trap carbon.

It is noted that the iron used in the carbon trap module 4200 can be safely disposed of or easily recycled. The carbon trap module 4200 and its contents may be heated independently, minimizing the heat loss from conduction to the carbon trap 400.

Figure 14:
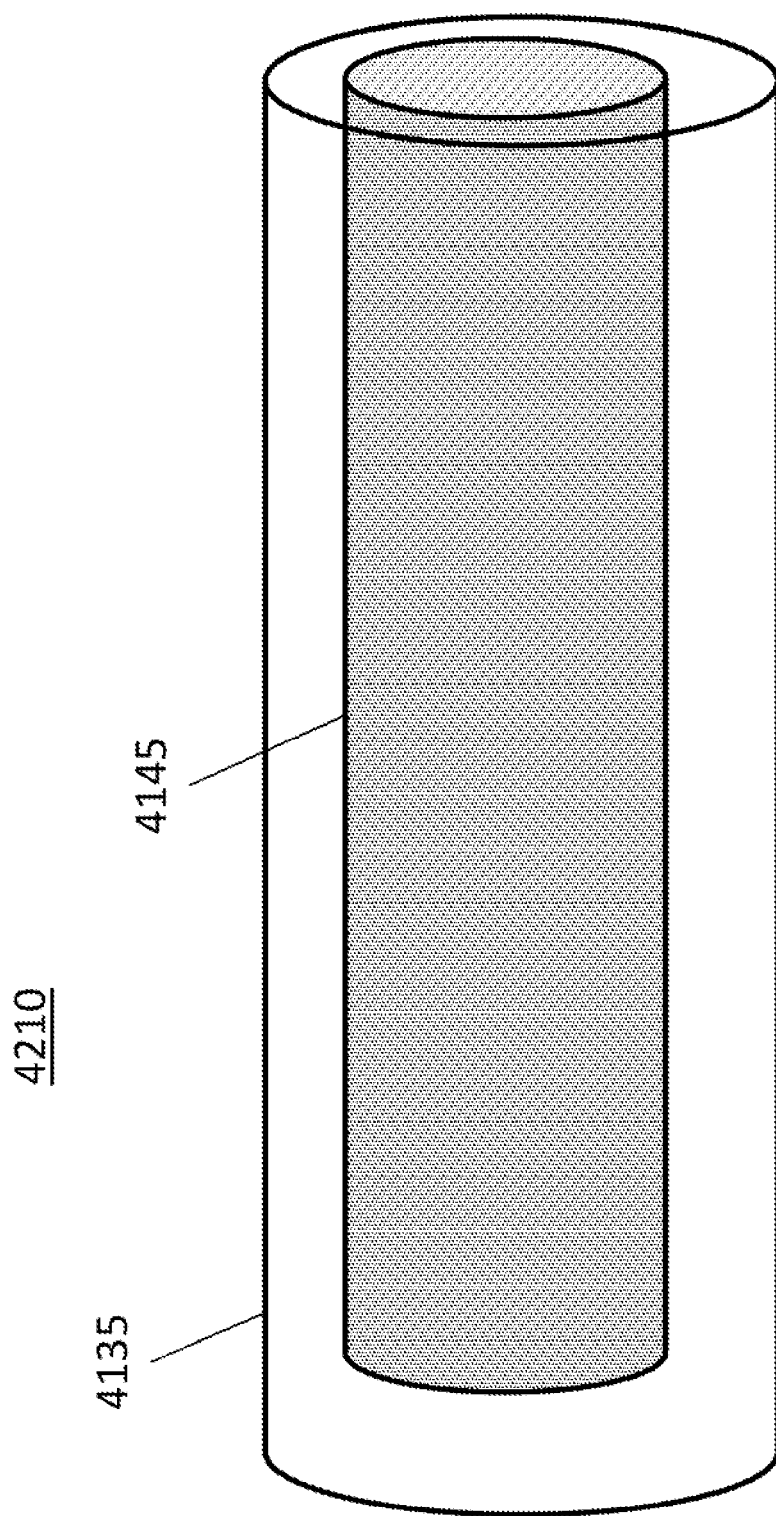
FIG. 14 illustrates another arrangement of a carbon trap module.

FIG. 14 illustrates another arrangement of a carbon trap module. As illustrated in FIG. 14, a carbon trap module 4210 includes an iron pipe or hollow cylinder 4135. The iron pipe or hollow cylinder 4135 includes, within its volume, a cartridge 4145 containing iron.

Optionally, the iron pipe or hollow cylinder 4135 may include, within its volume, a cartridge 4145 containing iron and copper. The cartridge 4145 and its contents may be heated independently, minimizing the heat loss from conduction to the carbon trap module 4210.

The iron pipe or hollow cylinder 4135 may be heated by a tubular heating element using electrical power. The heating element may be electrically insulated from the pipe iron pipe or hollow cylinder 4135.

In FIG. 14, the volume of the carbon trap is the inside volume of the iron pipe or hollow cylinder 4135. It is noted that the inside cross-sectional area of the iron pipe or hollow cylinder 4135 may be adjusted for gas flow considerations. It is further noted that the length of the iron pipe or hollow cylinder 4135 may be adjusted for absorption considerations.

Figure 15:
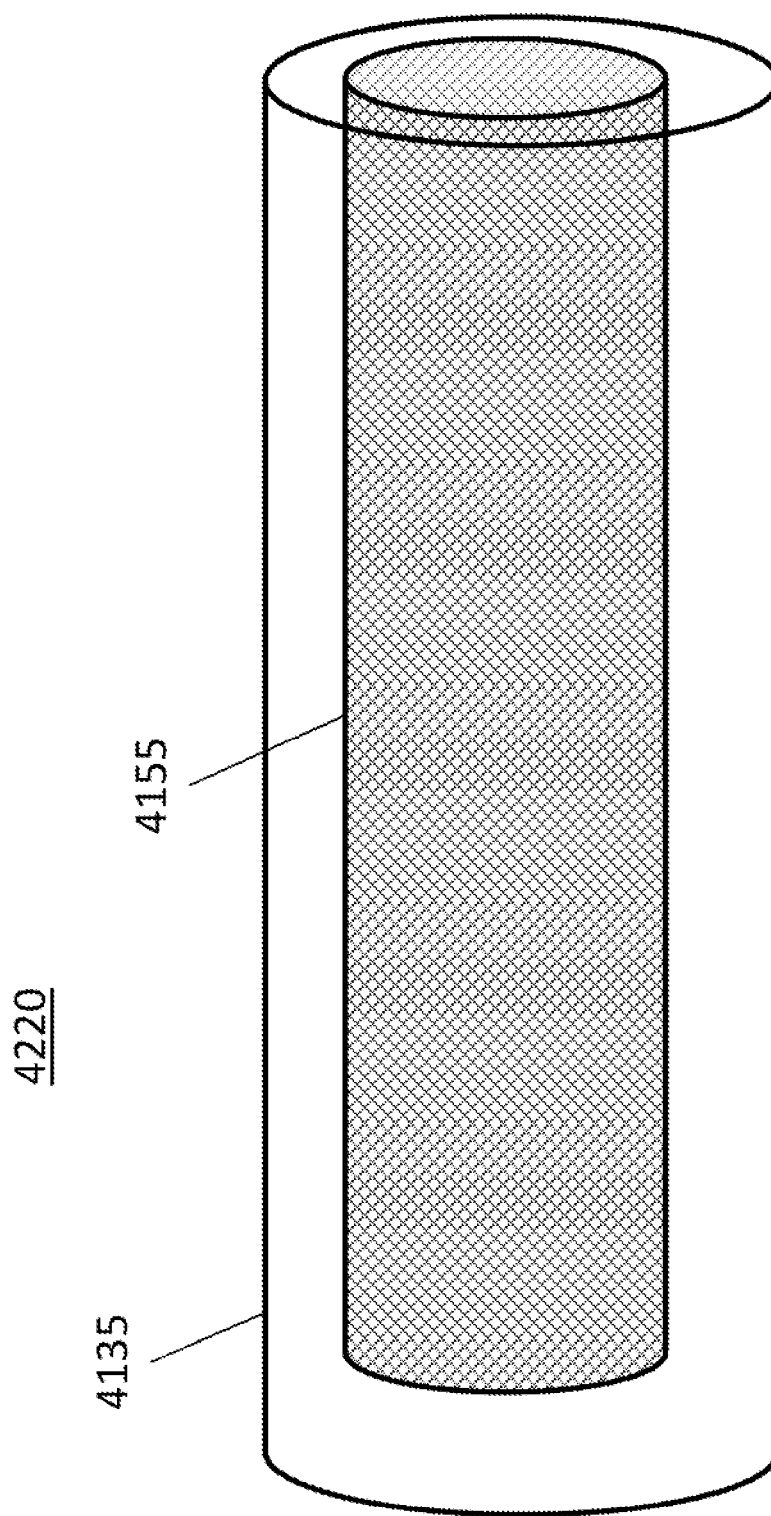
FIG. 15 illustrates another arrangement of a carbon trap module.

FIG. 15 illustrates another arrangement of a carbon trap module. As illustrated in FIG. 15, a carbon trap module 4220 includes an iron pipe or hollow cylinder 4135. The iron pipe or hollow cylinder 4135 includes, within its volume, steel (iron) wool 4155, which allows adequate flow of methane and/or carbon monoxide gasses.

Optionally, the iron pipe or hollow cylinder 4135 may include, within its volume, steel (iron) and copper wool 4155, which allows adequate flow of methane and/or carbon monoxide gasses.

The iron pipe or hollow cylinder 4135 may be heated by a tubular heating element using electrical power. The heating element may be electrically insulated from the pipe iron pipe or hollow cylinder 4135.

In FIG. 15, the volume of the carbon trap is the inside volume of the iron pipe or hollow cylinder 4135. It is noted that the inside cross-sectional area of the iron pipe or hollow cylinder 4135 may be adjusted for gas flow considerations. It is further noted that the length of the iron pipe or hollow cylinder 4135 may be adjusted for absorption considerations.

Figure 16:
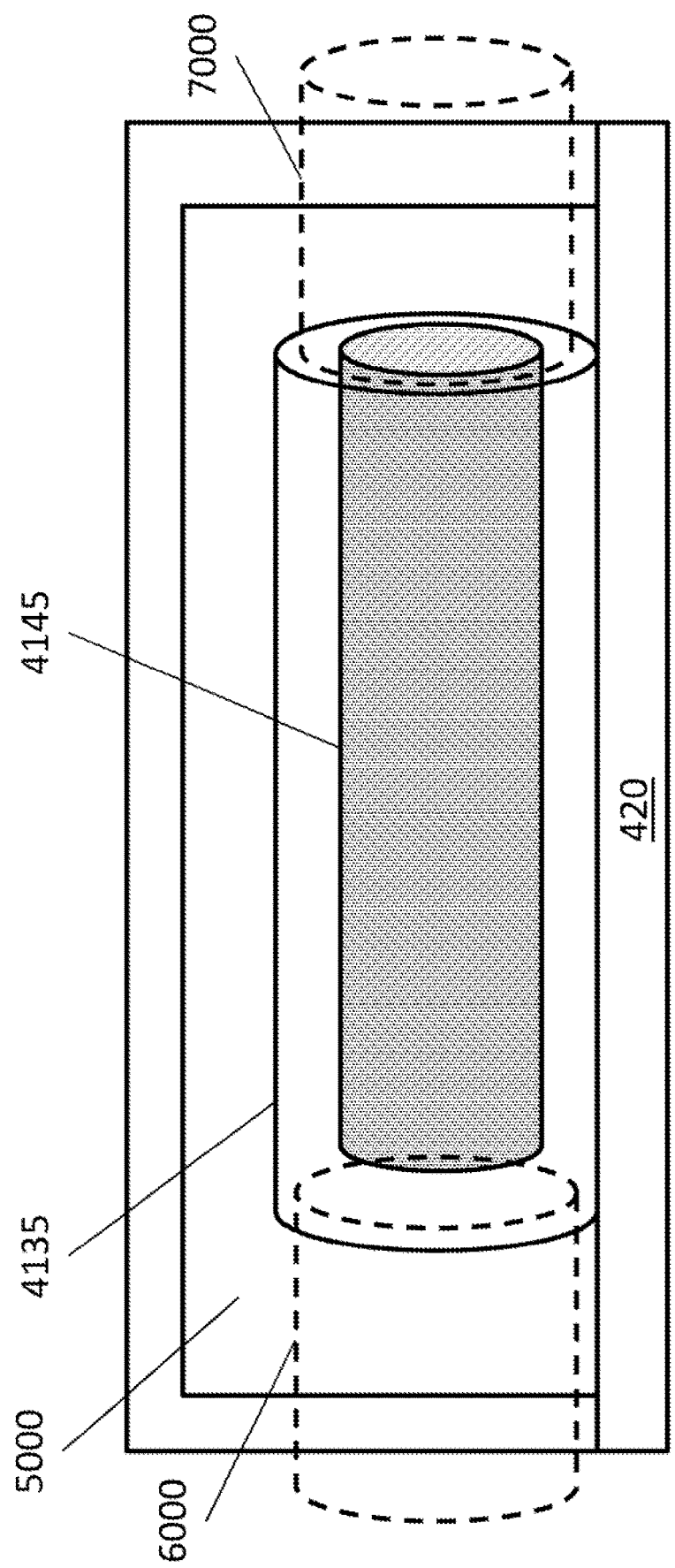
FIG. 16 illustrates another arrangement of a carbon trap.

FIG. 16 illustrates another arrangement of a carbon trap. As illustrated in FIG. 16, a carbon trap includes an iron pipe or hollow cylinder 4135. The iron pipe or hollow cylinder 4135 includes, within its volume, a cartridge 4145 containing iron.

Optionally, the iron pipe or hollow cylinder 4135 may include, within its volume, a cartridge 4145 containing iron and copper. The cartridge 4145 and its contents may be heated independently, minimizing the heat loss from conduction to the carbon trap.

The carbon trap also includes an evacuated volume 5000 and a heat source 420. The evacuated volume 5000 reduces heat loss. Additionally, the carbon trap includes an inlet tube or pipe 6000 for supplying carbon monoxide or methane to the carbon trap module, constructed of the iron pipe or hollow cylinder 4135 and cartridge 4145, and an outlet tube or pipe 7000 for outputting hydrogen from the carbon trap module, constructed of the iron pipe or hollow cylinder 4135 and cartridge 4145.

It is noted that the carbon trap of FIG. 16 may utilize the carbon trap module of FIG. 15.

Figure 17:
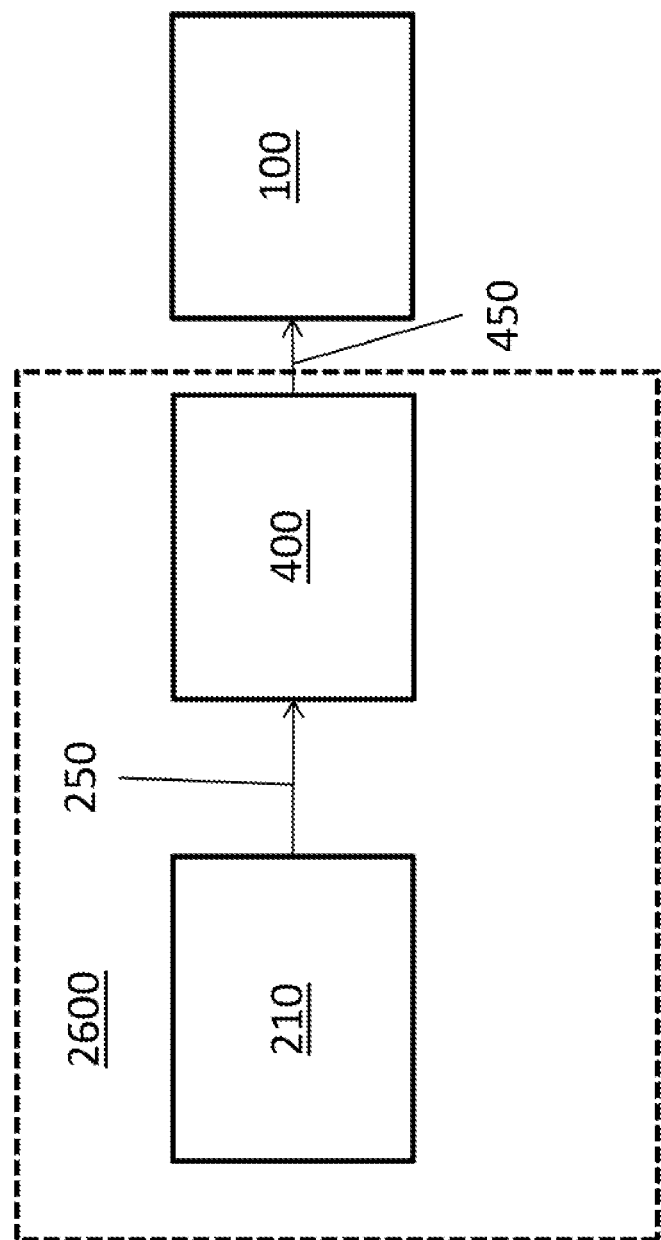
FIG. 17 illustrates another arrangement of a hydrogen generator that utilizes methane to create hydrogen to feed to a hydrogen fuel cell.

FIG. 17 illustrates another arrangement of a hydrogen generator 2500 that utilizes methane to create hydrogen to feed to a hydrogen fuel cell. As illustrated in FIG. 17, the hydrogen generator 2500 includes a source 210 of methane 250 that feeds a carbon trap 400. The carbon trap 400 captures the carbon from the methane 250 to create hydrogen 450. The carbon from the methane 250 is trapped in iron.

Hydrogen 450 is passed through the carbon trap 400 and is fed to a hydrogen fuel cell 100, which converts the hydrogen 450 into electricity.

In the various embodiments described above that utilizes methanol, an ammeter can be used in conjunction with a control valve, which controls the flow of methanol, to realize a maximum current to methanol consumption.

Figure 18:
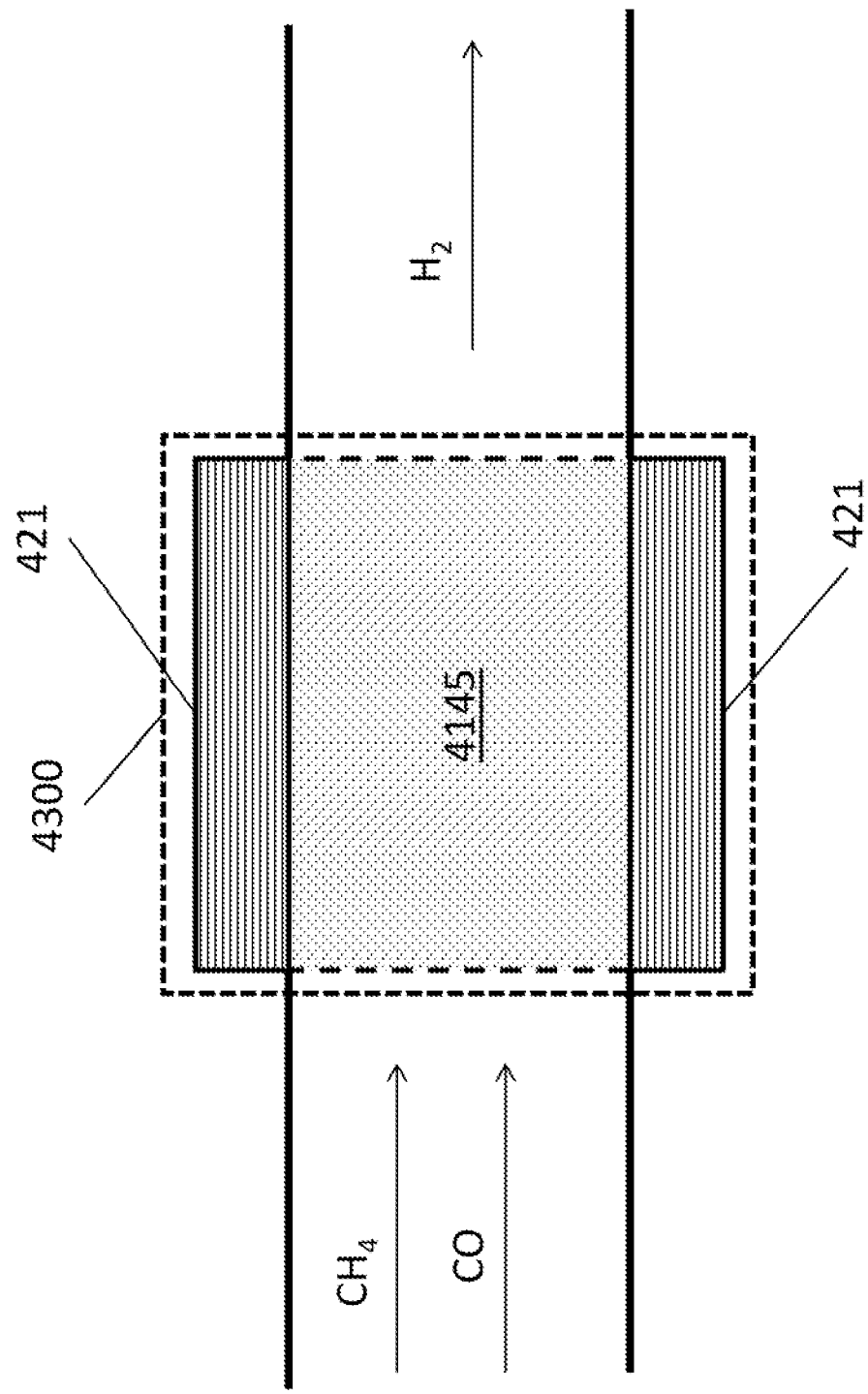
FIG. 18 illustrates another arrangement of a carbon trap.

FIG. 18 illustrates another arrangement of a carbon trap. As illustrated in FIG. 18, a carbon trap 4300 is fed methane ($CH_4$) and carbon monoxide (CO) by a supply pipe. The carbon trap 4300 includes an electrically insulted heat source 421 located around an outer surface of a cartridge 4145 containing iron and copper. The carbon trap 4300 may be cylindrical. The carbon trap 4300 includes, within its volume, the cartridge 4145 containing iron and copper. It is noted that the iron and copper may be iron wool and copper wool.

The methane ($CH_4$) and carbon monoxide (CO) interacts with the iron and copper contained in the cartridge 4145 such that the carbon and oxygen are removed and only hydrogen ($H_2$) exits the cartridge 4145.

Figure 19:
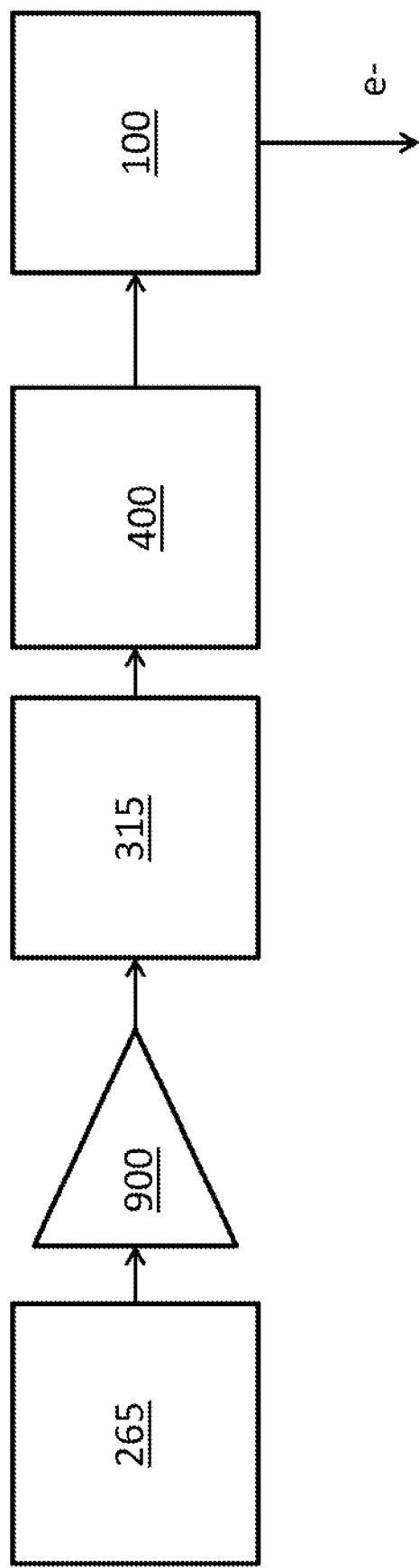
FIG. 19 illustrates a hydrogen fuel cell system for an electric vehicle.

FIG. 19 illustrates a hydrogen fuel cell system for use in an electric vehicle. As illustrated in FIG. 19, the hydrogen fuel cell system includes a source of methanol 265, which is pumped to a sprayer 900. The source of methanol 265 may be a storage tank on an electric vehicle. The stored methanol may be liquid "green" methanol.

The sprayer 900 sprays the methanol into a vaporizer 315 to produce a gaseous mixture of carbon monoxide and hydrogen. The gaseous mixture of carbon monoxide and hydrogen is fed to carbon trap 400 containing iron, which removes (physically captures) carbon from the carbon monoxide, to produce hydrogen and oxygen. The hydrogen and oxygen is fed to a hydrogen fuel cell 100 that utilizes the hydrogen to produce electricity (e–), while emitting oxygen to the atmosphere.

It is noted the carbon trap 400 may also include copper such that carbon trap 400 can remove (physically capture) carbon and oxygen from the methanol, to produce only hydrogen.

Figure 20:
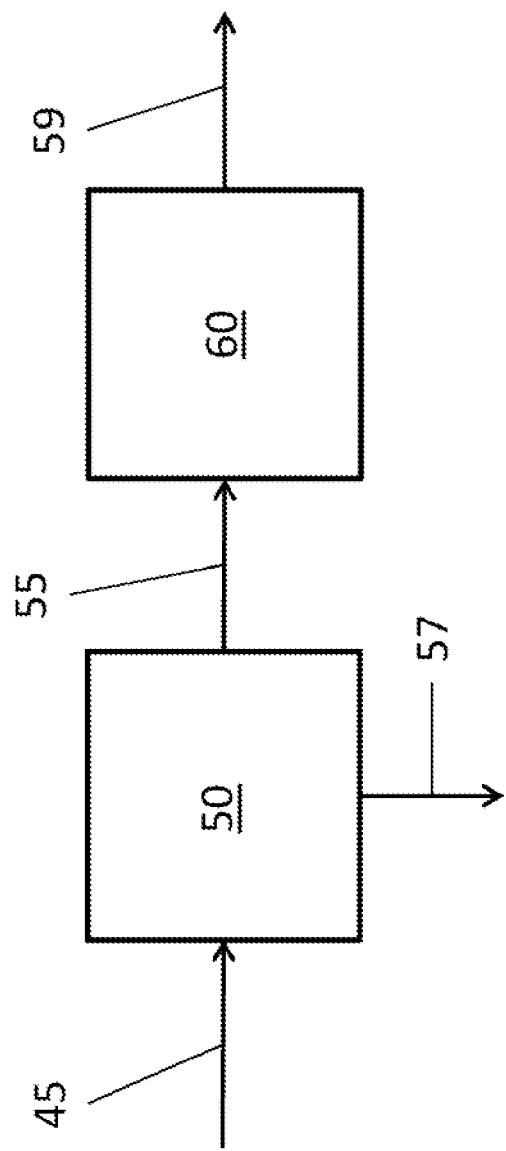
FIG. 20 illustrates a fractional condensing system for converting gaseous "red" methanol to gaseous hydrogen and "green" methanol.

FIG. 20 illustrates a fractional condensing system for converting gaseous "red" methanol to gaseous hydrogen and "green" methanol. As illustrated in FIG. 20, the fractional condensing system includes a first condenser 50 and a second condenser Gaseous "red" methanol 45 is fed into the first condenser 50. The gaseous "red" methanol 45, as discussed above, is gaseous methanol having large water (steam) content.

The first condenser 50 operates between the boiling point of water (100° C.) and just above the boiling point of methanol (64.7° C.). The first condenser 50 may operate below the boiling point of water (100° C.), but above the boiling point of methanol (64.7° C.).

Thus, the first condenser 50 condenses the excess water (steam) from the flow of gaseous "red" methanol 45. In other word, the first condenser 50 dries out the flow of gaseous "red" methanol 45, yielding gaseous methanol 55. The condensed water (57) can be drained off from the first condenser 50.

The gaseous methanol 55 is fed to the second condenser 60. The second condenser 60 operates between the boiling point of methanol (64.7° C.) and ambient temperatures. The second condenser 60 may operate below the boiling point of methanol (64.7° C.), but above the freezing point of methanol (−97.6° C.).

Thus, the second condenser 60 condenses the gaseous methanol 55 to produce liquid "green" methanol (59). The hydrogen from the second condenser 60 can be used by a proton exchange membrane hydrogen fuel cell system.

It is noted that the liquid "green" methanol (59) can be stored for distribution to a holding tank on an electric vehicle. The electric vehicle can use the "green" methanol, as needed to maintain the electric vehicle's stored energy (in the electric vehicle's batteries) and/or to operate the electric vehicle. The electric vehicle can use the vaporization of the liquid "green" methanol with a carbon trap to supply hydrogen to a hydrogen fuel cell and allow oxygen (by-product of the carbon trap) to be released into the environment.

The above-described fractional condensing system can be use in excess methane processes.

The above-described fractional condensing system can utilize all the methane available in any single source of methane. Thus, erratic wells and almost played out wells that have been capped, can used An erratic well which may have periods of no methane flow can be used, since the condensers will only recycle the water and not contaminate the stored "green" methanol.

The fractional condensing system uses all the methane available in any single source of methane when operating in the excess steam mode to create the maximum amount of "green" methanol.

The above-described fractional condensing system can also be used in the excess methane process since no excess steam is involved. Thus, the first condenser passes through the green methanol gas and the excess methane. The second condense condenses the green methanol to be stored for further uses. The excess methane gas can be passed into a carbon trap yielding hydrogen for feeding proton exchange membrane hydrogen fuel cell system to produce usable electrical power. The amount of "green" methanol produced is decreased by the amount of excess methane utilized.

The above-described fractional condensing system can utilize with a hybrid hydrogen fuel cell electric vehicle to extend the range of the hydrogen fuel cell due to the availability of the "green" methanol to create the needed hydrogen.

The liquid "green" methanol can be stored in the tank of a hybrid hydrogen fuel cell electric vehicle to provide electrical power to operate the hybrid hydrogen fuel cell electric vehicle and to recharge the hybrid hydrogen fuel cell electric vehicle's batteries. Thus, the range of the hybrid hydrogen fuel cell electric vehicle is determined by the power stored in the battery and the capacity of the storage tank of the liquid "green" methanol.

Additionally, the above-described fractional condensing system can utilize with a hybrid hydrogen fuel cell electric vehicle to reduce the size of the needed battery.

In the various embodiments described above, a carbon monoxide detector can be placed at the outlet of the carbon trap to measure the efficiency of the carbon trap to determine when the iron needs replacement or for preventative maintenance.

With the respect to the carbon traps described above, a carbon trap could be utilized in an exhaust system of an internal combustion engine to physically trap the carbon in carbon monoxide and produce oxygen, thereby reducing the production of toxic carbon monoxide and greenhouse gases.

It is noted that the various combinations described above can be utilized in a plant (factory) that uses methane supplied from a natural gas source, to produce methanol from the excess methane gas and put in a storage device or feed the excess methane to a carbon trap to prevent "flaring" of the excess methane.

As noted above, the efficiency of a carbon trap is determined by the rate which carbon is deposited on the trap's surface area by a flowing source of carbon monoxide and/or methane and by the amount of carbon that can be absorbed and stored in the trap's iron. Furthermore, the shape of the iron in the trap is not constrained. Thus, the design of the carbon trap should maximize the surface to volume ratio of the iron where possible since the iron may be replenished when desired.

It is further noted that the maximization of the surface to volume of the iron, could be accomplish by thin wire drawing, vapor deposition and other processes. It is noted that the iron may be constructed of steel wool made by a process similar to broaching. The maximization of the surface to volume of the copper can be realized by similar processes, such as thin wire drawing, vapor deposition, and copper wool.

It is also noted that diffusion of carbon in body centered cubic alpha iron is significantly faster than the diffusion in face centered cubic gamma iron at any temperature. Thus, the optimal maximum temperature for a carbon trap's operation occurs at a temperature where no gamma iron can exist. As noted above, that temperature is the eutectoid temperature, 772° C. Below this temperature, only alpha iron with carbon in interstitial site solution and cementite ($Fe_3C$) exists.

With respect to the various descriptions above, gasification is realized by supplying steam ($H_2O$ gas) to methane gas to create carbon monoxide and hydrogen. The chemical reaction is $CH_4 + H_2O$ (steam) $\rightarrow CO + 3H_2$.

Moreover, with respect to the various descriptions above, methanization is realized by cooling the carbon monoxide and hydrogen. The chemical reaction is $CO + 2H_2 + H_2 \rightarrow CH_3OH$ (liquid) $+ H_2$.

It is noted that methanol ($CH_3OH$) can be processed to produce carbon monoxide and hydrogen. The chemical reaction is $CH_3OH$ (liquid) $+ Heat \rightarrow CO + 2H_2$. The carbon monoxide and hydrogen can be processed by a carbon trap to capture the carbon. This carbon trap may also include an oxygen trap made of copper so that the only gas to pass therethrough is hydrogen.

It is noted that the above described embodiments can be modified to provide a source of methanol at a methane source, such as a landfill. The methane is used in the gasification/methanization process to produce methanol and hydrogen. Moreover, the methane can be passed directly into a carbon trap to produce hydrogen and oxygen. As noted above, the oxygen can also be trapped.

The hydrogen produced by the gasification/methanization process and the carbon trap process can be stored and used to power an offsite hydrogen fuel cell. The methanol can also be stored and used in other processes. This process can correct for methane flow, thereby eliminating flaring practices currently used at landfills.

Alternatively, the hydrogen produced by the gasification/methanization process and the carbon trap process can be fed directly to an onsite hydrogen fuel cell. This process can correct for methane flow, thereby eliminating flaring practices currently used at landfills.

The various embodiments described above can be utilized in an electric vehicle. However, electric vehicles powered solely by fuel cells alone have limitations.

It is noted that fuel cells are stackable like batteries. In parallel, a stack will increase the nominal voltage by multiples of the 0.7 volts of a single cell. In series the available current is increased.

Unfortunately, stacked fuel cells cannot store electrical energy as rechargeable batteries can because the electrical energy provided by a fuel cell is provided by the flow of fuel, whereas the electrical energy provided by batteries is based upon chemical behavior.

Thus, a combined system of fuel cells is appropriate for an electric vehicle. Such a system can be designed to facilitate fuel cell start up and the operation of the electric vehicle during this startup time. The fuel cells will then power the electric vehicle and recharge the batteries.

The flow of methanol can be controlled to maintain the battery charge for the vehicle's use. The advantages of this combined system over battery only systems are many.

The advantages may be (1) the reduced weight of the lithium batteries required compared to the weight of the fuel cell and methanol storage; (2) the pollution due to the manufacture and disposal of the unneeded and hazardous lithium batteries; (3) the possible explosion and fire of the lithium batteries due to user recharging; and/or (4) the refueling (methanol) at existing service stations rather than recharging at a presently limited number of electrical charging stations.

A hydrogen generator comprises a gasifier, upon receiving steam and methane, configured to convert the methane and steam into hydrogen and carbon monoxide; and a carbon trap, operatively connected to the gasifier, configured to capture carbon from the carbon monoxide and allow the hydrogen to pass therethrough; the carbon trap including iron.

The carbon trap may include copper to capture oxygen create by the capture of carbon from the carbon monoxide.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

The iron in the carbon trap may be iron wool and the copper in the carbon trap may be copper wool.

The carbon trap may include a heat source.

A hydrogen generator comprises a vaporizer, upon receiving heat and liquid methanol, configured to convert the liquid methanol into methane gas and water vapor; a condenser, operatively connected to the vaporizer, configured to cool methane gas and water vapor so as to condense the water vapor; and a carbon trap, operatively connected to the condenser, configured to capture carbon from the methane and allow the hydrogen to pass therethrough; the carbon trap including iron.

The vaporizer may include a heat source.

The carbon trap may include a heat source.

The carbon trap and the vaporizer may include a common heat source.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

A hydrogen generator comprises an input interface to receive methane; a carbon trap, operatively connected to the input interface to receive methane, configured to capture carbon from the methane to create hydrogen; a gasifier, operatively connected to the input interface to receive methane, the gasifier configured to receive steam and configured to mix the received methane with the received steam to create carbon monoxide and hydrogen; and a methanization module, operatively connected to the gasifier to receive carbon monoxide and hydrogen therefrom, configured to produce liquid methanol and hydrogen from the carbon monoxide and hydrogen produced by the gasifier; the carbon trap including iron.

The hydrogen generator may include valves configured to regulate a flow of methane to the carbon trap and the gasifier.

The carbon trap may include a heat source.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

A carbon trap comprises iron; and a heat source; the iron being configured in multiple parallel planes, forming channels therebetween; the multiple parallel planes being configured to increase a surface area to volume ratio of the iron.

The carbon trap may comprise copper.

The carbon trap may comprise an evacuated chamber around the iron.

A carbon trap comprises iron; and a heat source; the iron being configured to form a serpentine channel; the serpentine channel being configured to increase a surface area to volume ratio of the iron.

The carbon trap may comprise copper.

The carbon trap may comprise an evacuated chamber around the iron.

A carbon trap comprises an iron source; and a heat source; a first portion of the iron source being configured as a hollow cylinder; a second portion being configured as iron wool, the iron wool being located within the hollow cylinder.

The carbon trap may comprise copper.

The carbon trap may comprise an evacuated chamber around the iron.

The carbon trap may comprise copper wool located within the hollow cylinder.

A hydrogen generator, comprises a gasifier, upon receiving steam and methane, configured to convert the methane gas and steam into gaseous methanol, hydrogen, and methane gas; a condenser, operatively connected to the gasifier, configured to condense the gaseous methanol to liquid methanol and to allow the liquid methanol to be outputted therefrom; and a carbon trap, operatively connected to the condenser to receive the hydrogen and methane gas from the condenser, configured to capture carbon from the received methane gas to create hydrogen and to allow the hydrogen to pass therethrough; the carbon trap including iron.

The carbon trap may include copper to capture oxygen create by the capture of carbon from the carbon monoxide.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

The iron in the carbon trap may be iron wool and the copper in the carbon trap may be copper wool.

The carbon trap may include a heat source.

A hydrogen fuel cell system, comprises a hydrogen generator to generate hydrogen, and a hydrogen fuel cell, operatively connected to the hydrogen generator to receive hydrogen, to convert the received hydrogen to electricity; the hydrogen generator including a gasifier, upon receiving steam and methane, configured to convert the methane and steam into hydrogen and carbon monoxide, and a carbon trap, operatively connected to the gasifier, configured to capture carbon from the carbon monoxide and allow the hydrogen to pass therethrough; the carbon trap including iron.

The carbon trap may include copper to capture oxygen create by the capture of carbon from the carbon monoxide.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

The copper in the carbon trap may be copper wool.

The carbon trap may include a heat source.

A hydrogen fuel cell system, comprises a hydrogen generator to generate hydrogen, and a hydrogen fuel cell, operatively connected to the hydrogen generator to receive hydrogen, to convert the received hydrogen to electricity; the hydrogen generator including a gasifier, upon receiving steam and methane, configured to convert the methane gas and steam into gaseous methanol, hydrogen, and methane gas, a condenser, operatively connected to the gasifier, configured to condense the gaseous methanol to liquid methanol and to allow the liquid methanol to be outputted therefrom, and a carbon trap, operatively connected to the condenser to receive the hydrogen and methane gas from the condenser, configured to capture carbon from the received methane gas to create hydrogen and to allow the hydrogen to pass therethrough; the carbon trap including iron.

The carbon trap may include copper to capture oxygen create by the capture of carbon from the carbon monoxide.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

The copper in the carbon trap may be copper wool.

The carbon trap may include a heat source.

A hydrogen fuel cell system, comprises: a hydrogen generator to generate hydrogen, and a hydrogen fuel cell, operatively connected to the hydrogen generator to receive hydrogen, to convert the received hydrogen to electricity; the hydrogen generator including a vaporizer, upon receiving heat and liquid methanol, configured to convert the liquid methanol into methane gas and water vapor, a condenser, operatively connected to the vaporizer, configured to cool methane gas and water vapor so as to condense the water vapor, and a carbon trap, operatively connected to the condenser, configured to capture carbon from the methane and allow the hydrogen to pass therethrough; the carbon trap including iron.

The vaporizer may include a heat source.

The carbon trap may include a heat source.

The carbon trap and the vaporizer may include a common heat source.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap is iron wool.

A hydrogen fuel cell system, comprises a hydrogen generator to generate hydrogen, and a hydrogen fuel cell, operatively connected to the hydrogen generator to receive hydrogen, to convert the received hydrogen to electricity; the hydrogen generator including an input interface to receive methane; a carbon trap, operatively connected to the input interface to receive methane, configured to capture carbon from the methane to create hydrogen, a gasifier, operatively connected to the input interface to receive methane, the gasifier configured to receive steam and configured to mix the received methane with the received steam to create carbon monoxide and hydrogen, and a methanization module, operatively connected to the gasifier to receive carbon monoxide and hydrogen therefrom, configured to produce liquid methanol and hydrogen from the carbon monoxide and hydrogen produced by the gasifier; the carbon trap including iron.

The hydrogen fuel cell system may further comprise valves configured to regulate a flow of methane to the carbon trap and the gasifier.

The carbon trap may include a heat source.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

The carbon trap may include a heat source.

A carbon trap comprises a housing; and a replaceable carbon trap module; the replaceable carbon trap module including iron and a heat source; the iron being configured in multiple parallel planes, forming channels therebetween; the multiple parallel planes being configured to increase a surface area to volume ratio of the iron.

The carbon trap may further comprise copper.

The carbon trap may further comprise an evacuated chamber around the iron.

A carbon trap comprises: a housing; and a replaceable carbon trap module; the replaceable carbon trap module including iron and a heat source; the iron being configured to form a serpentine channel; the serpentine channel being configured to increase a surface area to volume ratio of the iron.

The carbon trap may further comprise copper.

The carbon trap may further comprise an evacuated chamber around the iron.

A carbon trap comprises a housing; and a replaceable carbon trap module; the replaceable carbon trap module including iron and a heat source; a first portion of the iron source being configured as a hollow cylinder; a second portion being configured as iron wool, the iron wool being located within the hollow cylinder.

The carbon trap may further comprise copper.

The carbon trap may further comprise an evacuated chamber around the iron.

The carbon trap may further comprise copper wool located within the hollow cylinder.

A hydrogen generator, comprises a source of methane; and a carbon trap, operatively connected to the source of methane, configured to capture carbon from the methane and allow the hydrogen to pass therethrough; the carbon trap including iron.

The vaporizer may include a heat source.

The carbon trap may include a heat source.

The carbon trap and the vaporizer may include a common heat source.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

A hydrogen fuel cell system, comprises a hydrogen generator to generate hydrogen, and a hydrogen fuel cell, operatively connected to the hydrogen generator to receive hydrogen, to convert the received hydrogen to electricity; the hydrogen generator including a source of methane, and a carbon trap, operatively connected to the source of methane, configured to capture carbon from the methane and allow the hydrogen to pass therethrough; the carbon trap including iron.

The vaporizer may include a heat source.

The carbon trap may include a heat source.

The carbon trap and the vaporizer may include a common heat source.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

A fractional condensing system for converting gaseous methanol having excess steam therein to a mixture of hydrogen and green methanol, comprising a source of gaseous methanol having excess steam therein; a first condenser, operatively connected to the source of gaseous methanol having excess steam therein, to condense the excess steam from the gaseous methanol having excess steam therein to produce a dried out the gaseous methanol; and a second condenser, operatively connected to the first condenser, to produce liquid green methanol.

The first condenser may operate between 100° C. and 64.7° C.

The first condenser may operate between below 100° C. and above 64.7° C.

The second condenser may operate below 64.7° C.

A hydrogen fuel cell system, comprising: a source of gaseous methanol having excess steam therein; a first condenser, operatively connected to the source of gaseous methanol having excess steam therein, to condense the excess steam from the gaseous methanol having excess steam therein to produce a dried out the gaseous methanol; a second condenser, operatively connected to the first condenser, produce liquid green methanol; a vaporizer, operatively connected to the second condenser, configured to produce carbon monoxide and hydrogen from the liquid green methanol; a carbon trap, operatively connected to the vaporizer to receive the carbon monoxide and hydrogen from the vaporizer, configured to capture carbon from the received carbon monoxide to capture the carbon from the carbon monoxide to create hydrogen and oxygen and to allow the hydrogen and oxygen to pass therethrough; and a hydrogen fuel cell, operatively connected to the carbon trap to receive the hydrogen, to convert the received hydrogen to electricity.

The first condenser may operate between 100° C. and 64.7° C.

The first condenser may operate between below 100° C. and above 64.7° C.

The second condenser may operate below 64.7° C.

The carbon trap may include iron.

The carbon trap may include a heat source.

The iron in the carbon trap may be configured in multiple parallel planes, forming channels therebetween; the multiple parallel planes being configured to increase a surface area to volume ratio of the iron.

The iron in the carbon trap may be configured to form a serpentine channel; the serpentine channel being configured to increase a surface area to volume ratio of the iron.

The carbon trap may include a removable/replaceable carbon trap module; the removable/replaceable carbon trap module including the iron.

The iron in the carbon trap may be iron wool.

It will be appreciated that several of the above-disclosed embodiments and other features and functions, or alternatives thereof, may be desirably combined into many other different systems or applications. Also, various presently unforeseen or unanticipated alternatives, modifications, variations, or improvements therein may be subsequently made by those skilled in the art which are also intended to be encompassed by the description above.

What is claimed is:

1. A fractional condensing system for converting gaseous methanol having excess steam therein to liquid green methanol, consisting of:
   a source of gaseous methanol having excess steam therein;
   a first condenser, operatively connected to said source of gaseous methanol having excess steam therein, to condense said excess steam from said gaseous methanol having excess steam therein to produce a dried out the gaseous methanol, said first condenser operating between 100° C. and 64.7° C.; and
   a second condenser, operatively connected to said first condenser, to produce liquid green methanol, said second condenser operating below 64.7° C.

2. A fractional condensing system for converting gaseous red methanol to a gaseous hydrogen, comprising:
   a source of gaseous methanol having excess steam therein;
   a first condenser, operatively connected to said source of gaseous methanol having excess steam therein, to condense said excess steam from said gaseous methanol having excess steam therein to produce a dried out the gaseous methanol; and
   a second condenser, operatively connected to said first condenser, to condense the dried out gaseous methanol to produce liquid green methanol;
   a vaporizer, operatively connected to said second condenser, configured to produce carbon monoxide and hydrogen from the liquid green methanol; and
   a carbon trap, operatively connected to said vaporizer to receive the carbon monoxide and hydrogen from said vaporizer, configured to capture carbon from the received carbon monoxide to create hydrogen.

3. The fractional condensing system, as claimed in claim 2, wherein said first condenser operates between 100° C. and 64.7° C.

4. The fractional condensing system, as claimed in claim 2, wherein said first condenser operates between below 100° C. and above 64.7° C.

5. The fractional condensing system, as claimed in claim 2, wherein said second condenser operates below 64.7° C.

6. The fractional condensing system, as claimed in claim 3, wherein said second condenser operates below 64.7° C.

7. The fractional condensing system, as claimed in claim 4, wherein said second condenser operates below 64.7° C.

* * * * *